United States Patent

Frost et al.

(10) Patent No.: US 9,884,943 B2
(45) Date of Patent: Feb. 6, 2018

(54) NO-RELEASING POLYMERS AND USES THEREOF

(71) Applicant: MICHIGAN TECHNOLOGICAL UNIVERSITY, Houghton, MI (US)

(72) Inventors: Megan Cecelia Frost, Hancock, MI (US); Genevieve E. Romanowicz, Houghton, MI (US)

(73) Assignee: Michigan Technological University, Houghton, MI (US)

( * ) Notice: Subject to any disclaimer, the term of this patent is extended or adjusted under 35 U.S.C. 154(b) by 0 days.

(21) Appl. No.: 14/429,663

(22) PCT Filed: Sep. 21, 2012

(86) PCT No.: PCT/US2012/056572
§ 371 (c)(1),
(2) Date: Mar. 19, 2015

(87) PCT Pub. No.: WO2014/046671
PCT Pub. Date: Mar. 27, 2014

(65) Prior Publication Data
US 2015/0247005 A1    Sep. 3, 2015

(51) Int. Cl.
C08G 77/392 (2006.01)
C08G 18/83 (2006.01)
C09D 127/22 (2006.01)
A61L 26/00 (2006.01)
C09D 175/04 (2006.01)
(Continued)

(52) U.S. Cl.
CPC ........ *C08G 77/392* (2013.01); *A61L 26/0014* (2013.01); *A61L 26/0019* (2013.01); *A61L 26/0066* (2013.01); *A61L 29/085* (2013.01); *A61L 29/16* (2013.01); *C08F 114/06* (2013.01); *C08G 18/3206* (2013.01); *C08G 18/4854* (2013.01); *C08G 18/6511* (2013.01); *C08G 18/6705* (2013.01); *C08G 18/833* (2013.01); *C08G 77/26* (2013.01); *C08G 77/388* (2013.01); *C09D 127/22* (2013.01); *C09D 175/04* (2013.01); *C09D 183/08* (2013.01); *A61L 2300/114* (2013.01); *A61L 2300/606* (2013.01)

(58) Field of Classification Search
None
See application file for complete search history.

(56) References Cited

U.S. PATENT DOCUMENTS

2002/0010146 A1    1/2002  Garvey et al.
2002/0115559 A1    8/2002  Batchelor et al.
(Continued)

FOREIGN PATENT DOCUMENTS

WO    2014/046671    3/2014

OTHER PUBLICATIONS

Zhang et al., "Nitric oxide releasing silicone rubbers with improved blood compatibility: preparation, characterization, and in vivo evaluation", Biomaterials 23 (2002) 1485-1494.*
(Continued)

*Primary Examiner* — Jianfeng Song
(74) *Attorney, Agent, or Firm* — Michael Best & Friedrich LLP

(57) ABSTRACT

The present invention provides stable, photosensitive polymers that release NO response to intensity and wavelength of light, methods of making such polymers and methods using such polymers.

10 Claims, 15 Drawing Sheets

(51) Int. Cl.
*A61L 29/08* (2006.01)
*A61L 29/16* (2006.01)
*C08F 114/06* (2006.01)
*C09D 183/08* (2006.01)
*C08G 77/26* (2006.01)
*C08G 77/388* (2006.01)
*C08G 18/48* (2006.01)
*C08G 18/65* (2006.01)
*C08G 18/67* (2006.01)
*C08G 18/32* (2006.01)

(56) References Cited

U.S. PATENT DOCUMENTS

2004/0224868 A1 11/2004 Meyerhoff et al.
2009/0233873 A1 9/2009 Smith et al.
2010/0303891 A1 12/2010 Lee et al.
2011/0059036 A1 3/2011 Arnold et al.
2011/0151000 A1 6/2011 Schultz et al.
2011/0159116 A1 6/2011 Reynolds et al.

OTHER PUBLICATIONS

Frost et al., "Synthesis, characterization, and controlled nitric oxide release from S-nitrosothiol-derivatized fumed silica polymer filler particles", J Biomed Mater Res A. Mar. 15, 2005;72(4):409-19.*
PCT/US2012/056572 International Search Report and Written Opinion dated Feb. 14, 2013 (15 pages).
PCT/US2012/056572 International Preliminary Report on Patentability dated Mar. 24, 2015 (2 pages).

* cited by examiner

NO-RELEASING POLYMERS AND USES THEREOF

STATEMENT REGARDING FEDERALLY SPONSORED RESEARCH

This invention was made with United States government support awarded by the National Science Foundation, Grant No. NSF-DMR-0906709-2009. The United States Government has certain rights in this invention.

CROSS-REFERENCE TO RELATED APPLICATIONS

This application is a national stage filing under 35 U.S.C. 371 of International Application No. PCT/US2012/056572, filed Sep. 21, 2012, which is incorporated herein by reference in its entirety.

BACKGROUND

Nitric oxide (NO) plays a critical role in the regulation of a wide variety of physiological processes. It is a potent inhibitor of platelet adhesion and aggregation, inhibits bacterial adhesion and proliferation, is implicated in mediating the inflammatory response to implanted medical devices, inhibits smooth muscle cell growth and proliferation, and is a neurotransmitter.

SUMMARY

In one embodiment, the invention provides a compound of Formula (I):

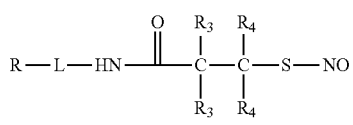

and racemates, enantiomers and diastereomers thereof;
wherein:
R is a polymer selected from the group consisting of polysiloxanes, polyvinylchlorides and polyurethanes;
L is a linker or a direct bond;
each $R_3$ is independently selected from H, aminocarbonyl, $C_{1-4}$ alkyl, aryl, heteroaryl, $C_{1-4}$ alkyl aryl, $C_{1-4}$ alkyl heteroaryl, cycloalkyl and heterocyclyl; and
each $R_4$ is independently selected from H, aminocarbonyl, $C_{1-4}$ alkyl, aryl, heteroaryl, $C_{1-4}$ alkyl aryl, $C_{1-4}$ alkyl heteroaryl, cycloalkyl and heterocyclyl.

In another embodiment, the invention provides a compound of Formula (II):

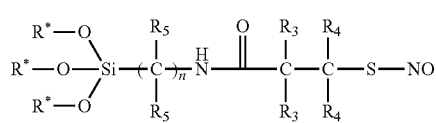

and racemates, enantiomers and diastereomers thereof;
wherein:
R* is a polysiloxane;
each $R_3$ is independently selected from H, aminocarbonyl, $C_{1-4}$ alkyl, aryl, heteroaryl, $C_{1-4}$ alkyl aryl, $C_{1-4}$ alkyl heteroaryl, cycloalkyl and heterocyclyl;
each $R_4$ is independently selected from H, aminocarbonyl, $C_{1-4}$ alkyl, aryl, heteroaryl, $C_{1-4}$ alkyl aryl, $C_{1-4}$ alkyl heteroaryl, cycloalkyl and heterocyclyl;
each $R_5$ is independently selected from H, $C_{1-4}$ alkyl, alkoxyl, $N(R_8)_2$ or —NHC(O)C($R_3$)$_2$C($R_4$)$_2$—S—NO;
each $R_8$ is independently selected from H and $C_{1-4}$ alkyl, with the proviso that $(R_8)_2$ cannot be $NH_2$; and
n is 1 to 6.

In yet another embodiment, the invention provides a compound of Formula (III):

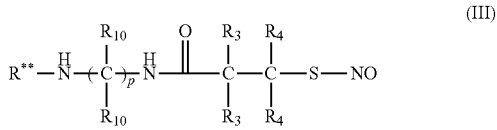

and racemates, enantiomers and diastereomers thereof;
wherein
R** is a polyvinylchloride;
each $R_3$ is independently selected from H, aminocarbonyl, $C_{1-4}$ alkyl, aryl, heteroaryl, $C_{1-4}$ alkyl aryl, $C_{1-4}$ alkyl heteroaryl, cycloalkyl and heterocyclyl;
each $R_4$ is independently selected from H, aminocarbonyl, $C_{1-4}$ alkyl, aryl, heteroaryl, $C_{1-4}$ alkyl aryl, $C_{1-4}$ alkyl heteroaryl, cycloalkyl and heterocyclyl;
each $R_{10}$ is independently selected from H, alkyl, halogen, alkoxy, carboxylic acid, acyl, aminocarbonyl, hydroxyl and amino;
p is 1 to 6.

In a further embodiment, the invention provides a compound of Formula (IV):

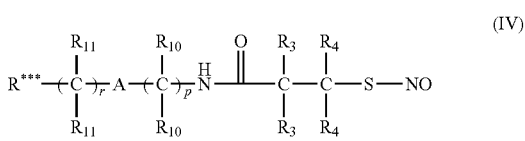

and racemates, enantiomers and diastereomers thereof;
wherein
R*** is a polyurethane;
each $R_3$ is independently selected from H, aminocarbonyl, $C_{1-4}$ alkyl, aryl, heteroaryl, $C_{1-4}$ alkyl aryl, $C_{1-4}$ alkyl heteroaryl, cycloalkyl and heterocyclyl;
each $R_4$ is independently selected from H, aminocarbonyl, $C_{1-4}$ alkyl, aryl, heteroaryl, $C_{1-4}$ alkyl aryl, $C_{1-4}$ alkyl heteroaryl, cycloalkyl and heterocyclyl;
each $R_{10}$ is independently selected from H, alkyl, halogen, alkoxy, carboxylic acid, acyl, aminocarbonyl, hydroxyl and amino;
each $R_{11}$ is independently selected from H, alkyl, halogen, alkoxy, carboxylic acid, acyl, aminocarbonyl, hydroxyl and amino;
A is NH or a direct bond;
p is 0 to 6; and
r is 0 to 6.

The invention also provides methods of making the compounds of Formulae (I)-(IV).

In addition, the method provides medical devices comprising the compounds of Formulae (I)-(IV).

Other aspects of the invention will become apparent by consideration of the detailed description and accompanying drawings.

DETAILED DESCRIPTION

Figure 1:
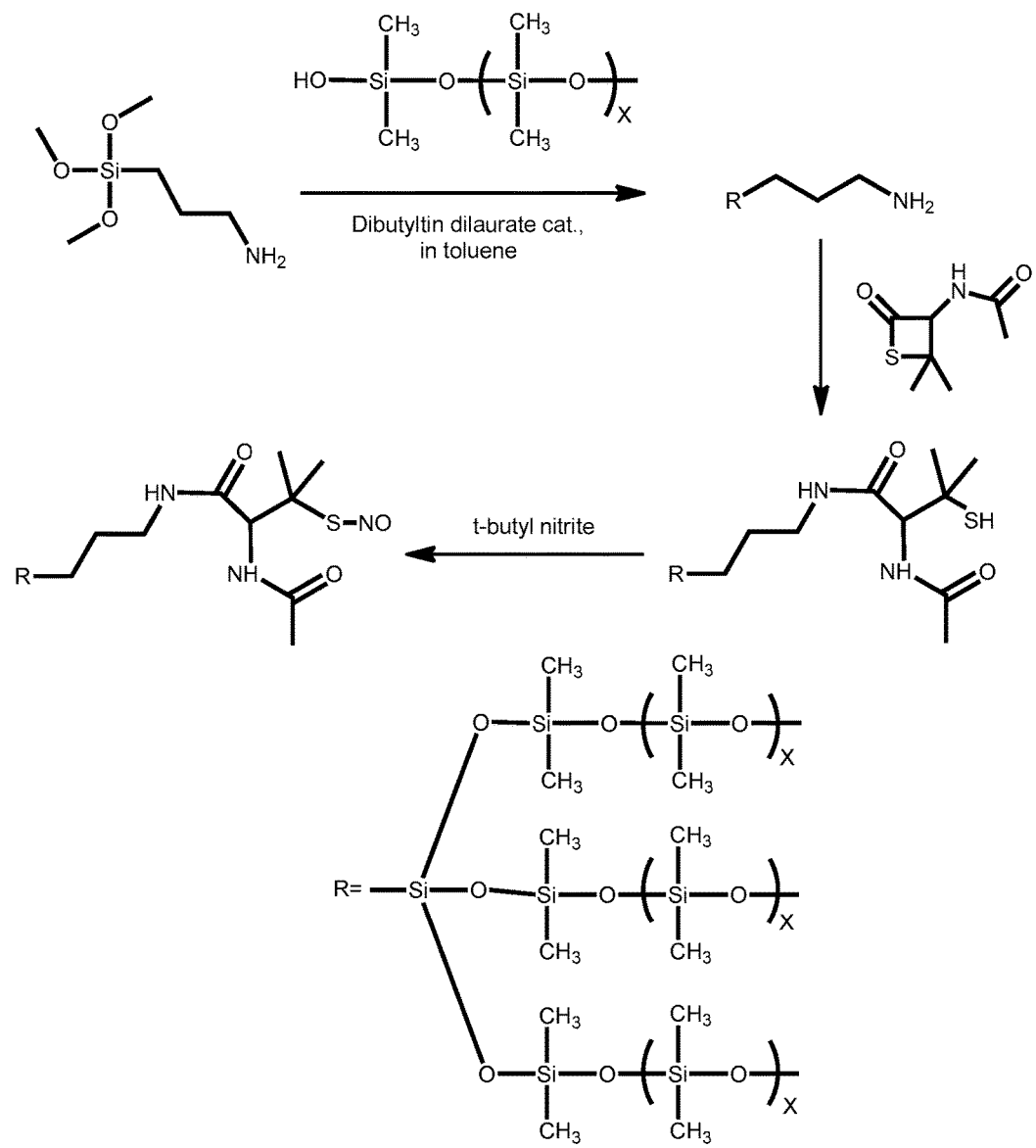
FIG. 1 shows a schematic of the synthesis of S-nitroso-N-acetyl-D-penicillamine covalently linked to polydimethylsiloxane (SNAP-PDMS).

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

S-Nitrosothiols (RSNOs) are a class of NO donors that are thought to serve as a reservoir and transporter of NO within biological systems. The stability of RSNOs is determined by the α and β substitution with respect to the sulfur atom. The S—NO bond of RSNOs can be cleaved to release NO by three known mechanisms: copper-ion mediation, direct reaction with ascorbate, and hemolytic cleavage of the S—NO bond by light (releasing NO and forming disulfide bonds from the radicals of the parent thiols).

Because of the great clinical promise of NO-releasing materials, there is a need for developing materials that will allow for dynamic control of NO-release after a biomedical device has been implanted. The present invention provides stable, photosensitive polymers that release NO in response to intensity and wavelength of light, methods of making such polymers and methods of using such polymers. The compounds of the present invention provide the ability to have a controllable, external on/off trigger for the generation of NO. Moreover, in certain embodiments, the compounds of the present invention do not have a memory, that is, they do not release NO for a period of time after the light source is turned off.

Definitions

As used herein, the term "alkyl" refers to an aliphatic hydrocarbon containing up to 18 carbon atoms including straight chain and branched chain groups. An "alkyl" group may be saturated or unsaturated. Examples include groups such as methyl, ethyl, n-propyl, isopropyl, n-butyl and the like. Alkyl groups may be substituted or unsubstituted. Suitably, an alkyl group may contain from 1-4 carbons or 1-6 carbons or 1-9 carbons. As an example, "$C_{1-4}$ alkyl" refers to alkyl groups containing one to four carbon atoms.

As used herein, the term "acyl" or "carbonyl" refers to the group —C(O)R" wherein R" is alkyl, alkenyl, alkyl alkynyl, aryl, heteroaryl, cycloalkyl, heterocycloalkyl, $C_{1-4}$ alkyl aryl or $C_{1-4}$ alkyl heteroaryl. $C_{1-4}$ alkylcarbonyl refers to a group wherein the carbonyl moiety is preceded by an alkyl chain of 1-4 carbon atoms. For example, $C_1$ alkylcarbonyl is —CH$_2$—C(O)—R.

As used herein, the term "alkoxyl" refers to the group —O—R" wherein R" is acyl, alkyl, aryl, cycloalkyl, heterocycloalkyl, heteroaryl, $C_{1-4}$ alkyl aryl or $C_{1-4}$ alkyl heteroaryl.

As used herein, the term "amino" refers to the group —NR'R' wherein each R' is, independently, hydrogen, alkyl, aryl, heteroaryl, $C_{1-4}$ alkyl aryl or $C_{1-4}$ alkyl heteroaryl. The two R' groups may themselves be linked to form a ring.

As used herein, the term "aminocarbonyl" refers to the group —NH—C(O)—R', wherein each R' is alkyl, aryl, heteroaryl, cycloalkyl, heterocycloalkyl, $C_{1-4}$ alkyl aryl or $C_{1-4}$ alkyl heteroaryl.

As used herein, the term "aryl" refers to an aromatic carbocyclic group of up to 10 carbons in the ring. Aryl groups may be either monocyclic or bicyclic. Suitable aryl groups include phenyl. The aryl group may be substituted or unsubstituted. As used herein, the term "carboxyl" refers to the group —C(=O)O—$C_{1-4}$ alkyl.

As used herein, the term "$C_{1-4}$ alkyl aryl" refers to $C_{1-4}$ alkyl groups having an aryl substituent such that the aryl substituent is bonded through an alkyl group. "$C_{1-4}$ alkyl aryl" may be exemplified by benzyl.

As used herein, the term "$C_{1-4}$ alkyl heteroaryl" refers to $C_{1-4}$ alkyl groups having a heteroaryl substituent such that the heteroaryl substituent is bonded through an alkyl group.

As used herein, the term "carbocyclic group" or "cycloalkyl" means a monovalent saturated or unsaturated hydrocarbon ring. Carbocyclic groups are monocyclic, or are fused, spiro, or bridged bicyclic ring systems. Monocyclic carbocyclic groups contain 3 to 10 carbon atoms, preferably 4 to 7 carbon atoms, and more preferably 5 to 6 carbon atoms in the ring. Bicyclic carbocyclic groups contain 8 to 12 carbon atoms, preferably 9 to 10 carbon atoms in the ring. Carbocyclic groups may be substituted or unsubstituted. Suitable carbocyclic groups include cyclopropyl, cyclobutyl, cyclopentyl, cyclohexyl, cyclohexenyl, and cycloheptyl. Carbocyclic groups are not aromatic.

As used herein, the term "halogen" or "halo" refers to fluoro, chloro, bromo or iodo moieties.

As used herein, the term "heteroaryl" or "heteroaromatic" refers to a monocyclic or bicyclic aromatic carbocyclic radical having one or more heteroatoms in the carbocyclic ring. A heteroaryl group contains up to 10 atoms in the ring. Heteroaryl may be substituted or unsubstituted. Suitable heteroaromatic groups include tetrazoyl, triazolyl; thienyl, thiazolyl, purinyl, pyrimidyl, pyridyl, and furanyl.

As used herein, the term "heteroatom" means an atom other than carbon in the ring of a heterocyclic group or a heteroaromatic group or the chain of a heterogeneous group. Heteroatoms are selected from the group consisting of nitrogen, sulfur, and oxygen atoms. Groups containing more than one heteroatom may contain different heteroatoms.

As used herein, the term "heterocarbocyclic group" or "heterocycloalkyl" or "heterocyclic" means a monovalent saturated or unsaturated hydrocarbon ring containing at least one heteroatom. Heterocarbocyclic groups are monocyclic, or are fused, spiro, or bridged bicyclic ring systems. Monocyclic heterocarbocyclic groups contain 3 to 10 carbon atoms, preferably 4 to 7 carbon atoms, and more preferably 5 to 6 carbon atoms in the ring. Bicyclic heterocarbocyclic groups contain 8 to 12 carbon atoms, preferably 9 to 10 carbon atoms in the ring. Heterocarbocyclic groups may be substituted or unsubstituted. Suitable heterocarbocyclic groups include epoxy, tetrahydrofuranyl, azacyclopentyl, azacyclohexyl, piperidyl, and homopiperidyl. Heterocarbocyclic groups are not aromatic.

As used herein, the term "hydroxy" or "hydroxyl" means a chemical entity that consists of —OH. Hydroxy groups may be free or protected.

As used herein, the term "linker" means a chain of n member atoms where n is an integer of from 1 to 15. A linker may be substituted or unsubstituted. A linker may be branched or unbranched.

As used herein, the term "member atom" means a carbon, silicon, nitrogen, oxygen or sulfur atom. Member atoms may be substituted up to their normal valence. If substitution is not specified the substituents required for valency are hydrogen.

As used herein, the term "ring" means a collection of member atoms that are cyclic. Rings may be carbocyclic, aromatic, or heterocyclic or heteroaromatic, and may be substituted or unsubstituted, and may be saturated or unsaturated. Ring junctions with the main chain may be fused or spirocyclic. Rings may be monocyclic or bicyclic. Rings contain at least 3 member atoms and at most 10 member atoms. Monocyclic rings may contain 3 to 7 member atoms and bicyclic rings may contain from 8 to 12 member atoms. Bicyclic rings themselves may be fused or spirocyclic.

Various groups are defined as optionally substituted. Suitable substituents include $C_{1-4}$ alkyl, aryl, heteroaryl, cycloalkyl, heterocycloalkyl, amino, cyano, halogen, alkoxy or hydroxyl.

Compounds

In one embodiment, the present invention provides a compound according to Formula (I):

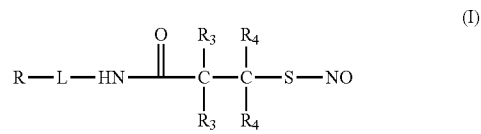

(I)

and racemates, enantiomers and diastereomers thereof;

wherein

R is a polymer selected from the group consisting of polysiloxanes, polyvinylchlorides and polyurethanes;

L is a linker or a direct bond;

each $R_3$ is independently selected from H, aminocarbonyl, $C_{1-4}$ alkyl, aryl, heteroaryl, $C_{1-4}$ alkyl aryl, $C_{1-4}$ alkyl heteroaryl, cycloalkyl and heterocyclyl; and each $R_4$ is independently selected from H, aminocarbonyl, $C_{1-4}$ alkyl, aryl, heteroaryl, $C_{1-4}$ alkyl aryl, $C_{1-4}$ alkyl heteroaryl, cycloalkyl and heterocyclyl.

In various embodiments, the linker is a cross-linking moiety such as (3-aminopropyl)trimethoxysilane, (3-aminopropyl)triethoxysilane or ethylenediamine. In certain embodiments, more than one nitrosothiol moiety can be bound to a single polymeric chain. In certain embodiments, more than one polymeric chain can be bound to a single nitrosothiol moiety, e.g. through a cross-linker.

In addition, various molecular weights of polymers may be used in the synthesis of these compounds. As one of ordinary skill in the art would understand, varying the molecular weight of the polymer alters the properties of the compound of Formula (I).

The invention also provides a compound according to Formula (II):

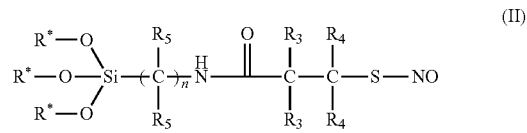

(II)

and racemates, enantiomers and diastereomers thereof;

wherein
R* is a polysiloxane;
each $R_3$ is independently selected from H, aminocarbonyl, $C_{1-4}$ alkyl, aryl, heteroaryl, $C_{1-4}$ alkyl aryl, $C_{1-4}$ alkyl heteroaryl, cycloalkyl and heterocyclyl;
each $R_4$ is independently selected from H, aminocarbonyl, $C_{1-4}$ alkyl, aryl, heteroaryl, $C_{1-4}$ alkyl aryl, $C_{1-4}$ alkyl heteroaryl, cycloalkyl and heterocyclyl;
each $R_5$ is independently selected from H, $C_{1-4}$ alkyl, alkoxyl, $N(R_8)_2$ or —NHC(O)C$(R_3)_2$C$(R_4)_2$—S—NO;
each $R_8$ is independently selected from H and $C_{1-4}$ alkyl, with the proviso that $(R_8)_2$ cannot be $NH_2$; and
n is 1 to 6.

Various polysiloxanes may be used in the present invention. For example, the silicone rubber may be a polydimethylsiloxane or a polydiethylsiloxane. In addition, various molecular weights are suitable for use in the present invention. For example, a higher weight polymer chains ($152 \times 10^6$ Daltons or 10,000 cSt) creates a compound that is more viscous due to greater chain entanglement and tend to lead to harder cured polymers, while lower molecular weight polymers ($1.6$-$1.7 \times 10^6$ Daltons or 700-800 cSt) tend to create compounds that are less viscous and cure to softer materials.

The nitrosothiol moiety may also be bound to a primary amine which is a substituent on the cross-linking moiety. Thus, more than one nitrosothiol moiety may be bound to a single cross-linked polysiloxane.

In addition, the invention provides a compound of Formula (III):

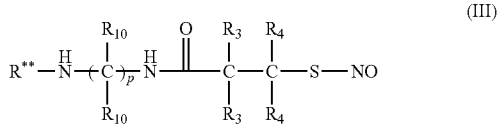

(III)

and racemates, enantiomers and diastereomers thereof;
wherein
R** is a polyvinylchloride;
each $R_3$ is independently selected from H, aminocarbonyl, $C_{1-4}$ alkyl, aryl, heteroaryl, $C_{1-4}$ alkyl aryl, $C_{1-4}$ alkyl heteroaryl, cycloalkyl and heterocyclyl;
each $R_4$ is independently selected from H, aminocarbonyl, $C_{1-4}$ alkyl, aryl, heteroaryl, $C_{1-4}$ alkyl aryl, $C_{1-4}$ alkyl heteroaryl, cycloalkyl and heterocyclyl;
each $R_{10}$ is independently selected from H, alkyl, halogen, alkoxy, carboxylic acid, acyl, aminocarbonyl, hydroxyl and amino;
p is 1 to 6.

Various polyvinylchlorides may be used in the synthesis of the compounds of Formula (III). Different molecular weights of the polyvinylchloride lead to different properties of the compound of Formula (III) as would be recognized by one of ordinary skill in the art. For example, low molecular weight PVC is used to manufacture rigid devices, while high molecular weight PVC is used to increase toughness and develop a matte surface finish. Flexibility of the these materials can also be adjusted with various plasticizers. In certain embodiments, about 2 to about 8% of the chlorines on a given polyvinylchloride are replaced with a nitrosothiol moiety.

The invention further provides a compound of Formula (IV):

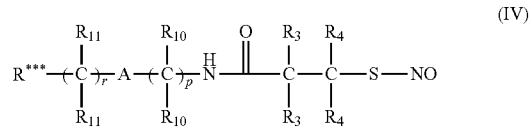

(IV)

and racemates, enantiomers and diastereomers thereof;
wherein
R*** is a polyurethane;
each $R_3$ is independently selected from H, aminocarbonyl, $C_{1-4}$ alkyl, aryl, heteroaryl, $C_{1-4}$ alkyl aryl, $C_{1-4}$ alkyl heteroaryl, cycloalkyl and heterocyclyl;
each $R_4$ is independently selected from H, aminocarbonyl, $C_{1-4}$ alkyl, aryl, heteroaryl, $C_{1-4}$ alkyl aryl, $C_{1-4}$ alkyl heteroaryl, cycloalkyl and heterocyclyl;
each $R_{10}$ is independently selected from H, alkyl, halogen, alkoxy, carboxylic acid, acyl, aminocarbonyl, hydroxyl and amino;
each $R_{11}$ is independently selected from H, alkyl, halogen, alkoxy, carboxylic acid, acyl, aminocarbonyl, hydroxyl and amino;
A is NH or a direct bond;
p is 0 to 6; and
r is 0 to 6.

Various polyurethanes may be used in the synthesis of the compounds of Formula (IV). In certain embodiments, about 2 to about 8% of H on the amine group in the urethane linkage of the polyurethane are replaced with the nitrosothiol moiety shown in Formula (IV). As one of ordinary skill in the art would understand the nitrosothiol moiety can be bound to any part of the polyurethane that contains a primary amine. For example, the nitrosothiol moiety may be bound to the isocyanate nitrogen in the polymer backbone through a linker. In another embodiment, the nitrosothiol moiety may be bound to a primary amine in a side chain of the polyurethane. Alternatively, the nitrosothiol moiety may be bound to the side chain through a linker. Other embodiments would be understood by those of ordinary skill in the art. More than one nitrosothiol moiety may be bound to a single segment of the polyurethane.

Methods of Synthesis

Compounds according to the present invention may be synthesized by a variety of methods. Briefly, a compound according to the present invention is synthesized by reacting a polymer containing a primary amine with a thiolactone to form a thiol-substituted polymer. The thiol-substituted polymer is reacted with an organo nitrite to form the nitrosothiol-substituted polymer.

In certain embodiments, the intermediates are not purified or isolated prior to continuing the reactions.

In certain embodiments, the polymer is a polysiloxane, a polyvinylchloride which as been reacted with an alkylenediamine to form a polyvinylchloride containing a primary amine, or a polyurethane which has been modified to contain a primary amine.

Suitable organo nitrites include, but are not limited to, t-butyl nitrite, n-butyl nitrite and iso-pentyl nitrite.

Suitable thiolactones include, but are not limited to,

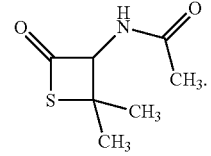

For example, compounds according to Formula (II) may be synthesized according to Scheme 1.

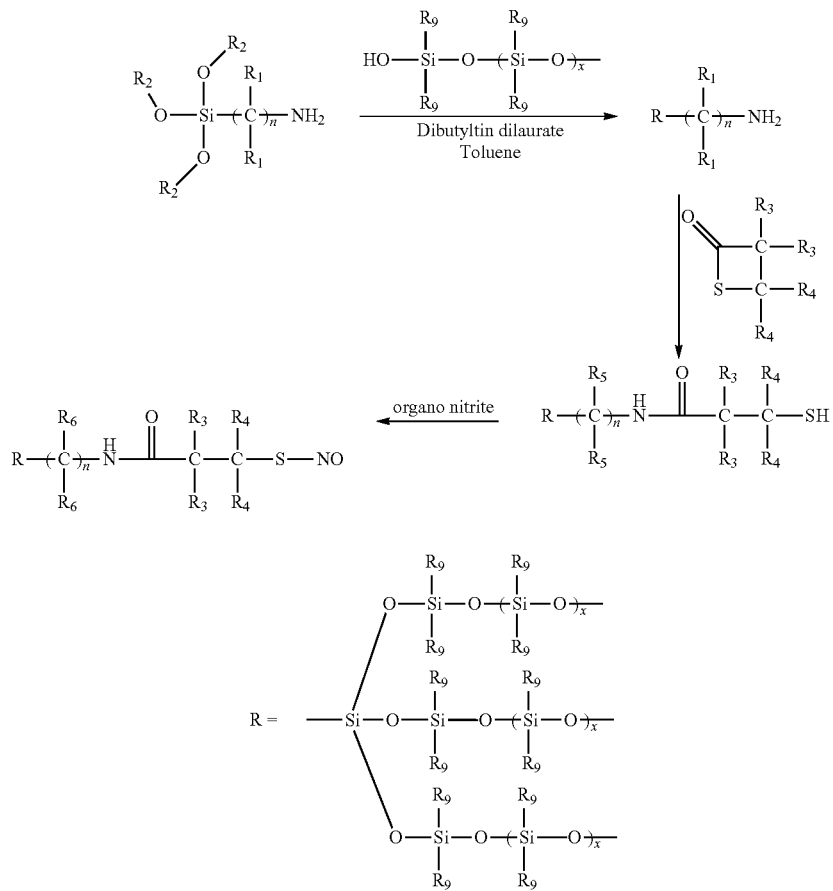

Scheme 1 wherein
each $R_1$ is independently selected from H, $C_{1-4}$ alkyl, $-N(R_7)_2$, and alkoxyl;
each $R_2$ is independently selected from $C_{1-4}$ alkyl;
each $R_3$ is independently selected from H, aminocarbonyl, $C_{1-4}$ alkyl, aryl, heteroaryl, $C_{1-4}$ alkyl aryl, $C_{1-4}$ alkyl heteroaryl, cycloalkyl and heterocyclyl;
each $R_4$ is independently selected from H, aminocarbonyl, $C_{1-4}$ alkyl, aryl, heteroaryl, $C_{1-4}$ alkyl aryl, $C_{1-4}$ alkyl heteroaryl, cycloalkyl and heterocyclyl;
each $R_5$ is independently selected from H, $C_{1-4}$ alkyl, alkoxyl, $N(R_8)_2$ or $-NHC(O)C(R_3)_2C(R_4)_2-S-H$ if $R_1$ was $NH_2$;

each $R_6$ is independently selected from H, $C_{1-4}$ alkyl, alkoxyl, $N(R_8)_2$ or $-NHC(O)C(R_3)_2C(R_4)_2-S-NO$ if $R_1$ was $NH_2$;

each $R_7$ is independently selected from H and $C_{1-4}$ alkyl;

each $R_8$ is independently selected from H and $C_{1-4}$ alkyl, with the proviso that $N(R_8)_2$ cannot be $NH_2$;

each $R_9$ is $C_{1-9}$ alkyl; and n is 1 to 6.

Compounds according to Formula (III) may be synthesized according to Scheme 2.

Scheme 2

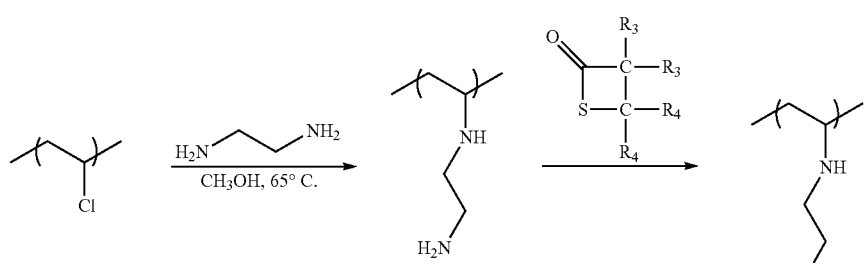

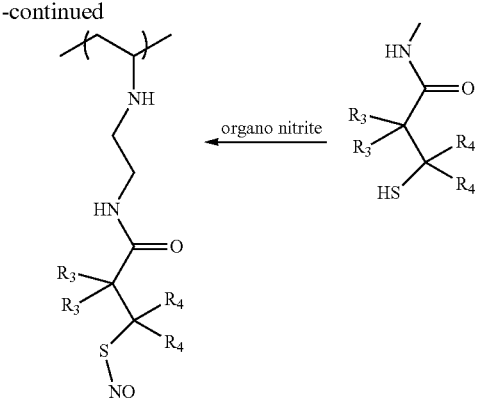

wherein $R_3$ and $R_4$ are as defined above.

As would be understood by one of ordinary skill in the art, various alkylene diamines can be used in the synthesis of compounds of Formula (III). Suitable alkylene diamines include, but are not limited to, ethylenediamine, 1,4-diaminebutane, or 1,5-diamino-2-methylpentane.

Compounds according to Formula (IV) may be synthesized according to Scheme 3.

Scheme 3

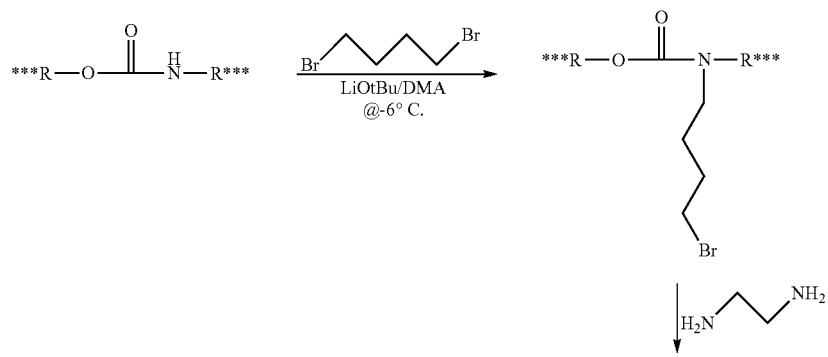

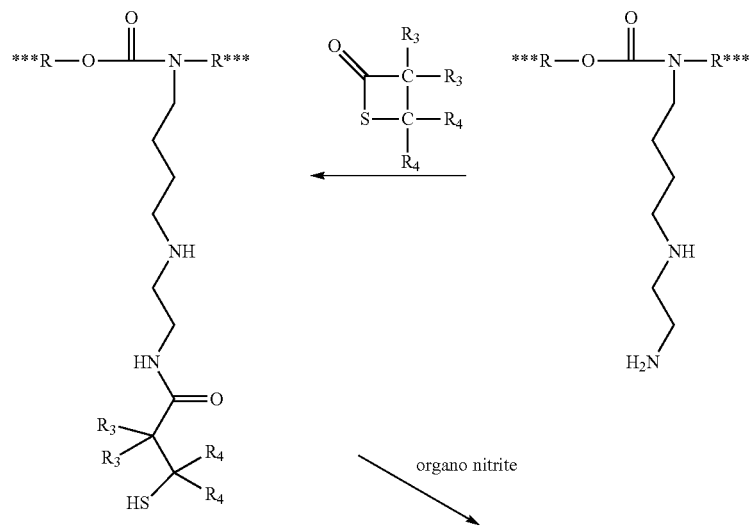

-continued

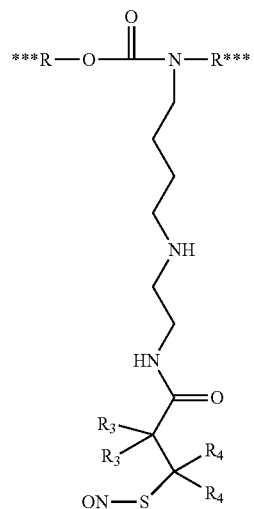

wherein R***, $R_3$, and $R_4$ are as defined above.

As would be understood by one of ordinary skill in the art, various alkylene diamines can be used in the synthesis of compounds of Formula (IV). Suitable alkylene diamines include, but are not limited to, ethylene diamine, 1,4-diaminebutane, or 1,5-diamino-2-methylpentane. In addition, one of ordinary skill in the art would recognize that various dibromoalkylenes may be used in the synthesis of compounds of Formula (IV). Suitable dibromoalkylenes include, but are not limited to, 1,4-dibromobutane, 1,2-dibromoethane, or 1,6-dibromohexane. If the compound of Formula (IV) contains a nitrosothiol moiety bound to a primary amine in the side chain, it is not necessary to use an alkylene diamine or a dibromoalkylene. In those situations, the thiolactone may be reacted with the polyurethane which contains a primary amine in the side chain to form the thiol which is then reacted with an organonitrite to form the nitrosothiol moiety.

Other methods of synthesizing the compounds of the formulae herein will be evident to those of ordinary skill in the art. Synthetic chemistry transformations and protecting group methodologies (protection and deprotection) useful in synthesizing the compounds are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Methods of Using the Compounds

The compounds disclosed herein may be used as coatings for medical devices and to fabricate medical devices. The compounds also may be used in methods for improving the biocompatibility of medical devices.

Most medical devices are made from materials that are not inherently compatible with blood and living tissue. When these devices come into contact with the blood and tissue of a host (e.g., when a device is implanted or at least partially inserted into a body), an inflammatory foreign body response may occur within the blood and tissues surrounding and adjacent to the outer surface of the device. During the foreign body response, macrophages and other immune cells in the tissue may become activated, and secrete proteolytic enzymes, proinflammatory and cytotoxic cytokines, reactive oxygen intermediates, leocotriens, and various other water soluble molecules characteristic of an immune response. Persistent or chronic exposure of tissues to these molecules may lead to inflammatory sequelae (e.g., pain, swelling and edema), cellular necrosis and scarring, which, in turn, may cause device migration, decreased device performance and/or complete device failure. Moreover, platelets may aggregate on the surface of the device, thereby increasing the risk of a severe clot and/or decreasing the performance of the device.

Nitric oxide (NO) has been implicated as an intracellular and intercellular messenger molecule that plays an important physiological role in anti-platelet aggregation anti-platelet activation, vascular relaxation, neurotransmission, and immune response. Synthetic materials that release low levels of NO more closely stimulate the natural activity of endothelial cells, and therefore, may have improved biocompatibility, and thus may be useful for coating or fabricating medical devices. Moreover, the NO ideally will be selectively releasable into the surrounding tissue or blood, such that the amount of NO released is controllable.

The compounds of this disclosure include a photosensitive S-nitrosothiol covalently attached to a polymer, where the S-nitrosothiol selectively releases NO as a function of the intensity and wavelength of incident light. The polymer may be selected so as to form compounds having varying mechanical properties. Some compounds may be used as coatings, films, or additives for other compositions, while some compounds may be used to fabricate medical devices themselves. For example, some compounds having relatively low molecular weight polymers may form liquids or gels that can be applied to the surface of a medical device as a coating or film, or that may be combined or blended with other components to form compositions. Some compounds having relatively high molecular weight polymers may form solid structures, and thus may be cast, or otherwise shaped to form a monolithic structure, such as may be used as to define the outer surface of an implantable or in-dwelling device. Specific examples include microfluidics, catheters, valves, punctual plugs, orthopedics and micro gaskets, pressure sensitive adhesives (PSAs), PSAs for transdermal systems, transdermal drug delivery, wound management applications to secure patches or dressings to the skin, adhesives, coatings on pacemakers, medical sealants, film-former, valve and tubing of a hydrocephalic shunt, intravenous bags and tubing and general purpose tubing.

Accordingly, the compounds of this disclosure may be used to coat or fabricate a wide variety of medical devices, including, but not limited to, microfluidics, catheters, stents, shunts, guide wires, balloons, valves, grafts, membranes, tubing, enteral nutrition bags, intravenous bags, dialysis bags, dressings and bandages, artificial skin, applications for securing dressings and bandages to the skin, materials for transdermal delivery systems (e.g., pressure sensitive adhesives, transdermal drug delivery systems, etc.), adhesives, sealants, sutures, bone anchors and screws, staples, protective and/or structural plates (e.g., bone plates), hip and joint implants, orthopedic and micro-gaskets, spine applications, fibers, pacemakers, electrical leads, biosensors, probes, electrodes, pumps, defibrillators, nerve stimulators, breast implants, artificial hearts, hospital bedding, inhalation masks, and the like. For example, compounds having the S-nitrosothiol attached to a polysiloxane may be used for microfluidics, catheters, implants, valves, punctual plugs, orthopedics and micro gaskets, pressure sensitive adhesives for transdermal systems, components of transdermal drug delivery systems, wound management applications to secure patches or dressings to the skin, adhesives, coatings on pacemakers, medical sealants, film-formers, and valves and tubing of a hydrocephalic shunt, among others. Compounds having the S-nitrosothiol attached to a PVC may be used for catheters, intravenous bags and tubing, enteral nutrition bags, dialysis bags and tubing in surgeries, artificial skin for emergency burn treatments, inhalation masks, injection molded single use devices that are pre-sterilized, and the like. Compounds having the S-nitrosothiol attached to a polyurethane may be used for catheters, total artificial heart, general purpose tubing, hospital bedding, surgical drapes, wound dressings, as well as in a variety of injection molded devices, foam wound dressings, composite wound dressings, surgical pads, anti-scar applications, pediatric devices, post-operative dressings, short-term implants, and the like.

Some of these devices (such as bandages, tubing, etc.) may be intended for use within or on the body of a patient in a location where ambient light will cause the S-nitrosothiol to automatically release NO. Others of these devices may be configured for implantation into the body of a patient, such that ambient light will not cause the S-nitrosothiol to automatically release NO. In these cases, an alternate light source may be required to stimulate NO release. For example, the medical device may include a light source, such as a wave guide, an optical fiber, or the like, that is positioned to direct light onto the surface of the medical device containing the S-nitrosothiol compound. The light source may be powered by a power source that is commonly associated with the medical device (e.g., the power source of a pacemaker, or glucose sensor, etc.), or that may be specially designed for use with the medical device in order to trigger the release of NO.

Compositions that are useful for coating or fabricating medical devices also may include a wide range of additional materials. For example, materials may be incorporated into the compositions that alter the physical and chemical properties of the composition, including, but not limited to, diluents, binders and adhesives, lubricants, disintegrants, colorants, bulking agents, flavorings, sweeteners, therapeutic agents, antifungals, antibiotics, plasticizers, buffers and the like. Such additional materials may be selected so as not to substantially interfere with the selective release of NO. The additional materials also may be selected so as to be biocompatible with a patient or host.

Compositions disclosed herein also may be used in methods for improving the biocompatibility of a medical device. For example, medical devices coated or formed with the compositions of this disclosure may prevent or inhibit the foreign body response, thrombosis, etc., at the device/tissue or device/blood interface. The method may include providing a medical device comprising a composition of this disclosure, and implanting or otherwise engaging the device with the blood or tissue of a patient. These devices may be placed in the body, for example, for a longer duration than a substantially similar device that is not fabricated or coated with the composition, with substantially little or no adverse effect to the patient.

It will be readily apparent to those skilled in the art that other suitable modifications and adaptations of the compounds and methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples which are merely intended only to illustrate some aspects and embodiments of the disclosure, and should not be viewed as limiting to the scope of the disclosure. The disclosures of all journal references, U.S. patents and publications referred to herein are hereby incorporated by reference in their entireties.

EXAMPLES

Example 1

Materials and Methods

Materials:
Silanol-terminated polydimethylsiloxane (viscosity 2,000 cSt) (PDMS) was purchased from Gelest, Inc. (Morrisville, Pa., USA). (3-Aminopropyl)trimethoxysilane, dibutyltin dilaurate, and concentrated hydrochloric acid were obtained from Aldrich Chemical Co. (Milwaukee, Wis., USA). N-acetyl-D-penicillamine was purchased from Fluka (St. Louis, Mo., USA). Tert-butyl nitrite, 90% tech. grade (Acros Organics) and toluene were obtained from Fisher Scientific (Pittsburgh, Pa., USA). Alfa Aesar acetic anhydride, magnesium sulfate ($MgSO_4$), and cyclam were purchased from VWR (West Chester, Pa., USA). House supply of 18 MΩ sterilized reverse osmosis water was used. Dow Corning RTV-3140 was used as a control (non-modified) PDMS (Ellsworth Adhesives, Germantown, Wis., USA).

Synthesis of thiolactone: A self-protected thiolactone was synthesized according to the procedure of Moynihan et al. (Preparation of novel S-nitroso compounds as potential slow release agents of nitric oxide in vivo. *J. Chem. Soc. Perkins Trans.* 1994, 1, 797-805). Briefly, 5 g of N-acetyl-D-penicillamine were dissolved in 10 mL pyridine and 10 mL of acetic anhydride were dissolved in 10 mL pyridine. Both solutions were ice cooled for 1 h and then combined. The reaction mixture was allowed to stir for 48 h at room temperature. A dark red-amber colour developed. Solvent was rotoevaporated at 50° C. to obtain a thick orange/amber coloured oil. This was dissolved in 30 mL chloroform and extracted with 30 mL 1 M HCl 3 times. The chloroform solution was dried with $MgSO_4$ and suction filtered to remove the drying agent. Chloroform was then removed with the rotoevaporator and resultant crystals were collected and rinsed with hexanes and suction filtration. Light yellow/white coloured, small needle-type crystals with a pungent odor were collected and allowed to air dry overnight.

Synthesis of SNAP-PDMS: FIG. 1 shows the synthetic scheme of SNAP-PDMS. 1.6 g of silanol-terminated PDMS was dissolved in 4 mL of toluene with the aid of vortex mixing. 0.3 g of (3-Aminopropyl)trimethoxysilane were dissolved in 2 mL toluene. The PDMS and (3-Aminopropyl)trimethoxysilane were combined and vortex mixed. 1.0 mL of a stock solution containing 20 mg of dibutyltin dilaurate in 20 mL of toluene was added to the PDMS/(3-Aminopropyl)trimethoxysilane solution and vortex mixed immediately. The PDMS was continually stirred and allowed to cross-link at room temperature for 24 h. 50 mg of the thiolactone were dissolved in 1 mL of toluene and 2 mL of the cross-linked PDMS solution were added and stirred for 24 h. The thiol groups were then nitrosated with t-butyl nitrite to form S-nitroso-N-acetyl-D-penicillamine that is covalently linked to the PDMS cross-links (SNAP-PDMS). A dark green colour developed after approximately 15 minutes and the reaction was allowed to continue for approximately 45 minutes while protected from light before the SNAP-PDMS was used. The t-butyl nitrite was first cleaned by extraction with 15 mM aqueous cyclam. 1 mL of t-butyl nitrite was vigorously shaken with 2 mL of 15 mM cyclam. The cyclam was replaced for a total of 3 extraction steps. Freshly cleaned t-butyl nitrite was stored in an amber vial in the refrigerator. 0.5 mL of cleaned t-butyl nitrite were added to 3 mL SNAP-PDMS. SNAP-PDMS films were cast by pipetting 2 mL of the SNAP-PDMS solution in 2.4 cm dia. polytetrafluoroethylene (PTFE) rings on a PTFE base plate and allowed to cure overnight protected from light. Dark green films (approximately 200 μm thick) were obtained that released NO upon illumination.

Figure 2:
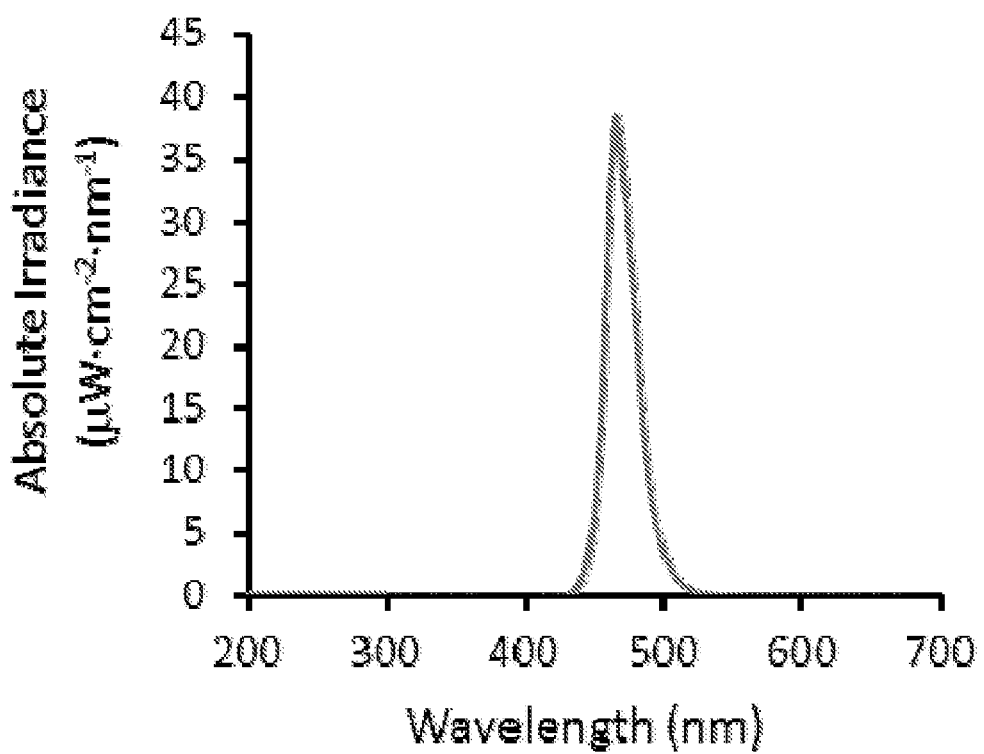
FIG. 2 shows a spectrum of light emitted from the C503B-BAN-CY0C0461 LED, $\lambda_{dominant}$=470 nm with a resistance set at 830Ω, and 6V applied potential.

Photoinitiation of NO Release: An in-house LED light source was utilized to initiate NO release from SNAP-PDMS. A C503B-BAN-CY0C0461 LED, $\lambda_{dominant}$=470 nm (470 nm LED) (Mouser Electronics, Mansfield, Tex., USA) in series with a voltage source and resistance of 138Ω operated at different applied potentials (0, 3, 4.5 and 6 V that correspond to 0, 3, 12 and 20 mA current, respectively) was used as the light source to release NO. FIG. 2 shows the spectrum of light emitted from the C503B-BAN-CY0C0461 LED, $\lambda_{dominant}$=470 nm with a resistance set at 830Ω, and 6V applied potential.

Nitric Oxide Release Measurements: Nitric oxide release was measured using a Sievers 280i Nitric Oxide Analyzer (GE Instruments, Boulder, Colo., USA) using 200 mL/min nitrogen carrier gas. SNAP-PDMS films were cut into 7 mm diameter discs and placed in a cell holder with the LED epoxied on the inner side of the top of the amber sample holder. Amber cells were used to exclude ambient radiation from the SNAP-PDMS test discs. The LED illuminated the broad side of a SNAP-PDMS disc from a distance of 5 cm.

Example 2

Generation of a SNAP-PDMS Polymer

Figure 3:
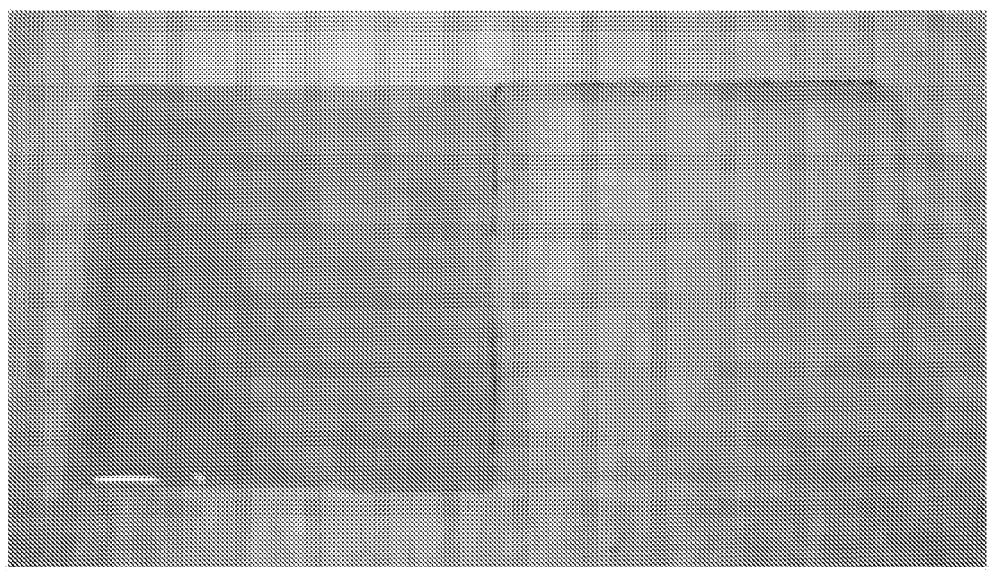
FIG. 3 shows photographs of (a) the SNAP-PDMS after a film has been cast and cured compared to (b) a control PDMS (Dow Corning RTV-3140) film that did not contain the modified cross-linking agent.

A SNAP-PDMS polymer was made as described in Example 1. Briefly, a primary amine group was incorporated into the PDMS by using a cross-linking agent that contains an aminopropyl group. This cross-linking agent was previously used to form diazeniumdiolate containing silicone rubber. The cross-linked PDMS was then reacted with the self-protected thiolactone that reacted with the primary amine groups to form an amide bond with the N-acetyl-D-penicillamine and resulted in a free thiol group that formed the corresponding S-nitrosothiol. Upon nitrosation, the SNAP-PDMS developed a dark green colour indicative of the formed S-nitroso-N-acetyl-D-penicillamine. FIG. 3 shows photographs of the SNAP-PDMS (a) after a film was cast and cured compared to (b) a control PDMS (Dow Corning RTV-3140) film that did not contain the modified cross-linking agent (i.e., no primary amine groups present in the PDMS) that was mixed with the thiolactone for 24 h and followed the same procedure for nitrosation that was used with the SNAP-PDMS. No green colour developed, indicating that the S-nitrosothiol was not formed.

Figure 4:
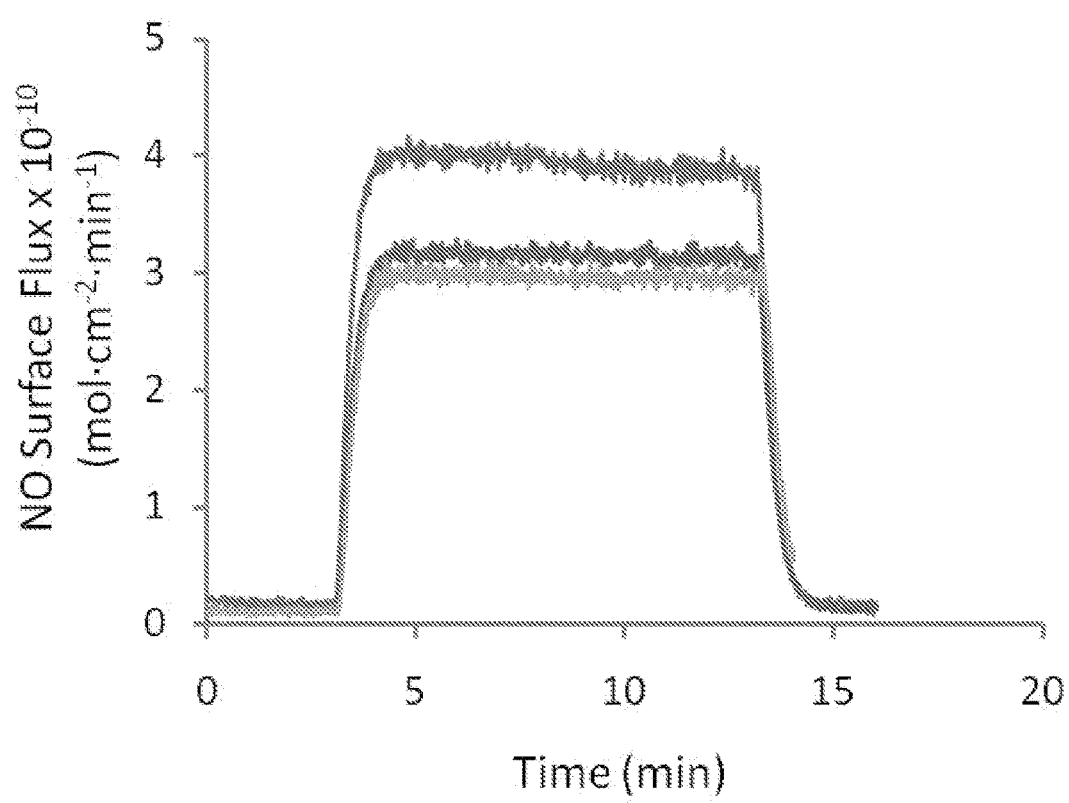
FIG. 4 shows a representative plot of surface flux of NO generated from 3 different 7 mm diameter discs of SNAP-PDMS exposed to light from the C503B-BAN-CY0C0461 LED, $\lambda_{dominant}$=470 nm with 6 V applied potential with 830Ω resistance (corresponds to 20 mA).
Figure 5:
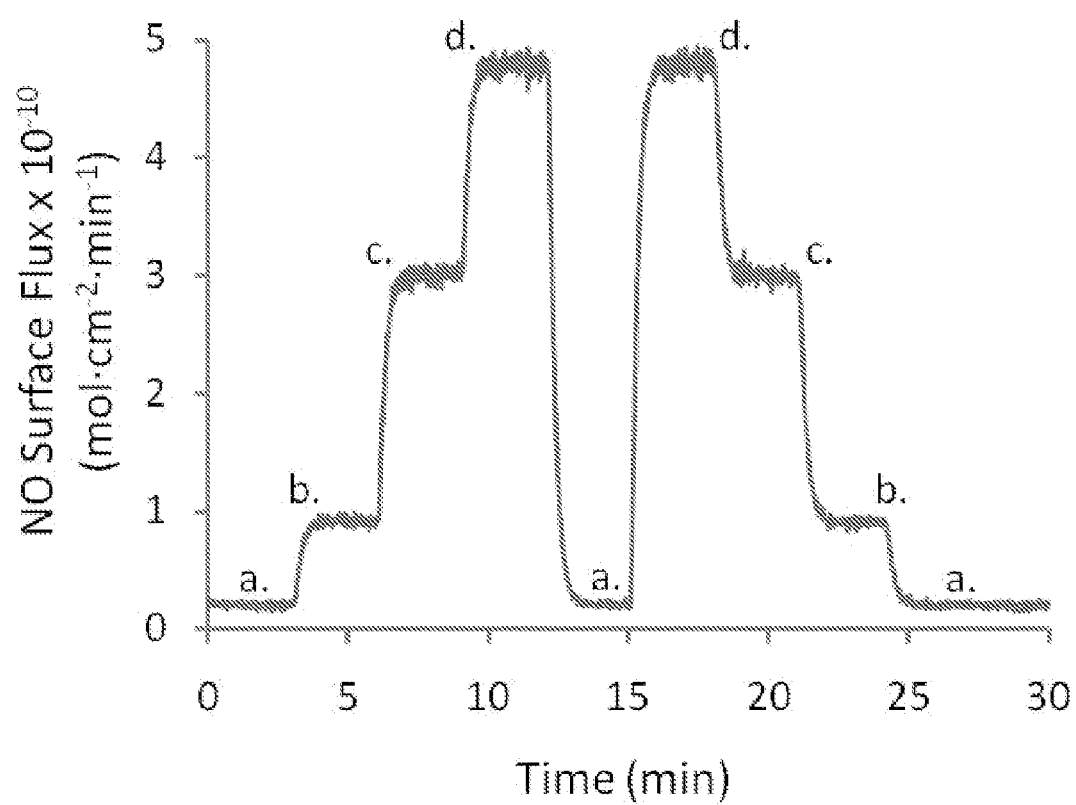
FIG. 5 shows variable NO generation from a 7 mm diameter disc of SNAP-PDMS when the applied potential is changed to the LED. Shown are results in the absence of light (a) and 3 V (b), 4.5 V (c), and 6 V (d) of applied potential.
Figure 6:
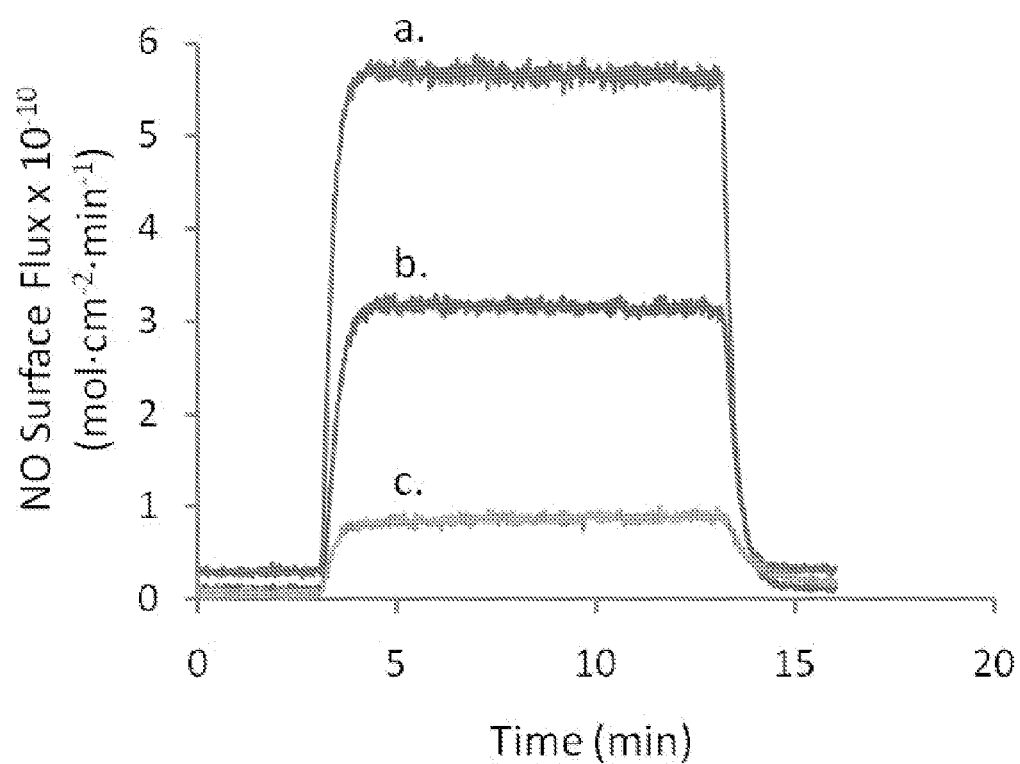
FIG. 6 shows NO generation from the films upon storage in the dark at 4° C. after (a) 13 (b) and 57 days (5.7±0.06 and 3.2±0.05×10$^{-10}$ mol·cm$^{-2}$·min$^{-1}$ respectively). The films were then kept in the dark at room temperature and after (c) 297 days, were still generating NO (0.8±0.02×10$^{-10}$ mol·cm$^{-2}$·min$^{-1}$) (averaged over 10 min of NO release).

The SNAP-PDMS polymer was examined for its ability to control NO release, thereby allowing different durations and levels of NO to be delivered on a continually variable basis as needed for a given biological application. FIG. 4 shows the surface flux of NO generated from 3 different 7 mm diameter discs of SNAP-PDMS exposed to light from the C503B-BAN-CY0C0461 LED, $\lambda_{dominant}$=470 nm with 6 V applied potential (corresponds to 20 mA). The average NO surface flux was 3.34±0.46×10-10 mol·cm$^{-2}$·min$^{-1}$ (n=3). The variability in surface flux of NO generated was due in part to variable thicknesses of the films cast. FIG. 5 shows the variable NO generation from a 7 mm diameter disc of SNAP-PDMS when the applied potential was changed to the 470 LED. In the absence of light, virtually no NO was generated (trace a), as the amount of light that impinged on the SNAP-PDMS was increased by stepping through 3, 4.5, and 6 V of applied potential (traces b, c, and d), the surface flux of NO increased from 0.2±0.04, 0.9±0.02, 3.1±0.03, to 4.8±0.05×10-10 mol·cm$^{-2}$·min$^{-1}$ respectively (averaged over 1 min of release). This was well within the range of physiologically relevant NO generation estimated to be produced by endothelial cells (1-4×10$^{-10}$ mol·cm$^{-2}$·min$^{-1}$). FIG. 6 shows NO generation from the films upon storage in the dark at 4° C. after 13 and 57 days (traces a and b, 5.7±0.06 and 3.2±0.05×10-10 mol·cm$^{-2}$·min$^{-1}$ respectively). The films were then kept in the dark at room temperature, and after 297 days (trace c), they were still generating NO (0.8±0.02×10-10 mol·cm$^{-2}$·min$^{-1}$, averaged over 10 min of NO release). This demonstrated that the SNAP-PDMS film was robust enough to continue generating measurable NO for 297 days even under these non-optimal storage conditions.

The SNAP-PDMS material showed great promise as a controlled NO releasing material. Using light as an external trigger to release NO allowed precise control of turning NO on and off as well as increasing or decreasing NO flux as desired. This may be used as a research tool to probe precisely what levels of NO are needed to achieve specific physiological responses.

The SNAP-PDMS material was used as a substrate upon which cells can be grown, in order to begin to understand how the level and duration of NO imposed on the cells affects different cell types.

Additionally, SNAP-PDMS has been coated on polymethylmethacrylate (PMMA) optical fibers and used to very effectively generate NO with precise control when the fiber was illuminated with the same C503B-BAN-CY0C0461 LED, $\lambda_{dominant}$=470 nm. These coated fibers will be used to begin to probe in vivo responses to intravascular and subcutaneous sensors.

Example 3

Materials and Methods

Optical Fiber Preparation:

Unjacketed, unbuffered 500 μm multimodal plastic optical fiber (POF) was obtained from Moritex (San Jose, Calif.). The cladding in the portion of fiber intended for NO generation was removed. For this removal process, the region to be declad was submerged into pure acetone for 45 seconds, after which the fiber was removed and wiped sharply several times with a lint free tissue. The acetone was then neutralized by submerging the declad region into deionized water followed by isopropyl alcohol to end the etching process and leave a clean, oil free fiber with the original physical and chemical properties of the core being maintained. Complete cladding removal was confirmed using a micrometer and a light microscope.

SNAP-PDMS synthesis: Hydroxy-terminated 2,000 cSt polydimethyl siloxane (PDMS) was purchased from Gelest, Inc., (Morrisville, Pa.). Aminopropyl trimethyoxysilane was obtained from Sigma-Aldrich Co. (St. Louis, Mo.). Dibutyltin dilaurate and toluene were purchased from Sigma-Aldrich Co. (St. Louis, Mo.). Tert-butylnitrite (90% technical grade) (t-BuONO) was purchased from Acros Organics (Geel, Belgium). All reagents were used as received except the t-BuONO. The t-BuONO was extracted over 15 mM aqueous cyclam (Sigma-Aldrich, St. Louis, Mo.) in order to remove copper added as a stabilizing agent prior to use.

Detailed synthesis of this material has been described in Gierke et al. (S-Nitroso-N-acetyl-D-penicillamine covalently linked to polydimethylsiloxane (SNAP-PDMS) for use as a controlled photoinitiated nitric oxide release polymer. *Science and Technology of Advanced Materials* 2011, 12 055007). Briefly, 1.6 g of hydroxy-terminated PDMS was mixed with 0.3 g of aminopropyl trimethoxysilane, 2.4 mg of dibutyltin dilaurate, and 8 mL of toluene. The solution was stirred for 24 hours to cross link the PDMS. A self-protected thiolactone was synthesized by according to the method by Moynihan et al. (*J. Chem. Soc. Perkins Trans.* 1994, 1: 797-805). 50 mg of this thiolactone were then added to 1 mL of toluene and 2 mL of the crosslinked PDMS. This solution was stirred for an additional 24 hours to allow the thiol-containing compound to react with the primary amine groups present on the cross-linking agent. 1 mL of cleaned t-BuONO was then added at which point the polymer was protected from light and placed on a shaker table for 30 minutes which resulted in an emerald green polymer. This color change was indicative of the formation of SNAP linked to the PDMS backbone (final product is SNAP-PDMS). After shaking, 9 coats of the polymer were then immediately applied via dip coating onto the optical fibers utilized in this work and allowed to fully cure in the dark under ambient conditions. Final coating thickness was approximately 100 μm.

Coupling an excitatory light to the optical fiber: A 500 μm bare fiber adapter with an SMA connector was obtained from Fiberplus International (Milford, Pa.). The fiber to be tested was placed within the connector and polished using a four step wet sanding process typical to the fiber optic industry. SMA receptacles were obtained from Amphenol (Wallingford, Conn.) and used to couple LEDs to fibers fixed within bare fiber adapters. A VAOL-5GSBY4 LED ($\lambda_{dominant}$=460 nm) was obtained (VCC Optoelectronics, San Marcos, Calif.) and fixed within the SMA receptacle following xyz active alignment using a spectrometer to ensure maximal coupling efficiency.

Directing the excitatory LED: The excitatory LED was incorporated into a microcontroller-based wireless end device. Firmware was written to control an access point (AP) that communicated with the end device (ED) to enable it to produce the biasing voltage and drive current to the excitatory LED through an operational amplifier in accordance with a sequence received wirelessly. The AP and ED were built upon MSP430FG4618 microcontrollers (MCU) on Experimenter's Boards (Texas Instruments, Dallas, Tex.). Chipcon CC2500 software defined radio daughterboard were also obtained from Texas instruments (Dallas, Tex.) and connected to the Experimenter's Board. Firmware incorporating the SimpliciTI WSN stack (Texas Instruments, Dallas, Tex.) was developed and written to the MCUs to allow the AP to act as a liaison between an investigator using a PC and the wireless ED. A PC based application was created to allow an investigator to program a sequence directing the drive current to the LED on a temporal basis by modulating the voltage produced by the operational amplifier on the end device. A calibration equation for the excitatory LED was calculated and applied to the data sent to the end-device.

Measuring dominant wavelength shift with current: The excitatory LED was fixed within an SMA receptacle and connected to the drive circuitry described previously. Two 0.5 neutral density filters were placed in-line with and in between the LED and a CCD spectrometer in order to prevent saturation. The output from the light was directed by the wireless system described above and the spectral shift in the dominant wavelength was measured as drive current was varied.

Measuring integrity of wave-guide properties: The excitatory LED was fixed within an SMA receptacle and actively aligned as previously described. The LED was then connected to a length of the same type of PMMA optical fiber used during experimentation. The distal end of the PMMA fiber was then connected to a CCD spectrometer using a bare fiber adapter. A biasing voltage and drive current were supplied to the LED and the transmitted intensity was recorded. The cladding was then removed from a section of fiber as previously described and a second spectrum was recorded.

Measuring NO surface flux: The optical fiber was connected at one end to the excitatory LED attached to the ED through the method previously described. The SNAP-PDMS coated end was placed within a sample holder connected to a Seivers Nitric Oxide Analyzer (NOA) 280i (GE Instruments, Boulder, Colo.) at 22° C. The entire sample holder was protected from ambient light. 200 mL/min nitrogen was used as the sweep gas. To convert parts per billion (ppb) of NO to surface flux of NO, the instrument was calibrated with acidified sodium nitrite to obtain the constant of $1.05 \times 10^{-13}$ mol·sec$^{-1}$·ppb$^{-1}$. The surface area of the NO releasing region of the fibers was calculated to be 0.473 cm$^2$ based on a 3 cm length of fiber that was declad and coated with SNAP-PDMS. All surface flux data was presented as $10^{-10}$ mol·cm$^{-2}$·min$^{-1}$ to be in the same order of magnitude and time units previously published and estimated to be physiologically relevant.

Disc preparation for solution initiated decomposition and temperature affects: 50 μL of SNAP-PDMS solution were cast onto 12 mm diameter circular glass slip covers and allowed to cure for 24 hours. A top coat of Dow Corning RTV-3140 was cast by placing 25 μL of the RTV-3140 solution (0.5 g/10 mL of toluene) on top of cured SNAP-PDSM and allowed to cure overnight. Film thickness was measured to be 300 μm.

Example 4

Cladding Removal Creates a Region of Radiant Excitance

Figure 7:
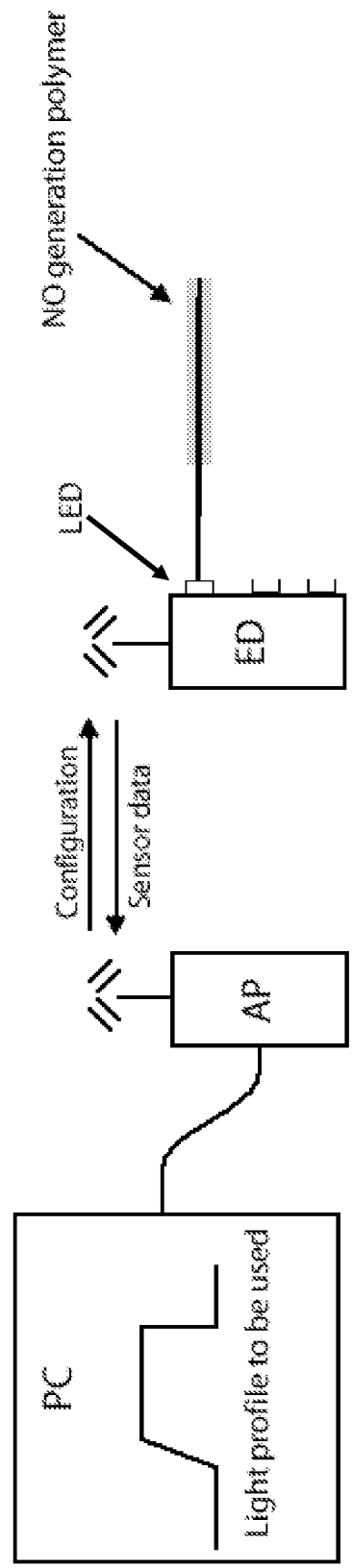
FIG. 7 shows a schematic diagram of the wireless NO generating platform developed that allows an investigator to direct NO generation from coated optical fibers with precise control over the pattern and duration of NO released.

The overall design of the photoinitiated NO releasing system is shown in FIG. 7. A computer program was written that allowed a defined pattern of light to be generated through an access point (AP) that wirelessly communicated with an end device (ED) that contained a VAOL-5GSBY4 LED ($\lambda_{dominant}$=460 nm) with a PMMA optical fiber coated with a polymer that contained a photosensitive NO donor.

Figure 8:
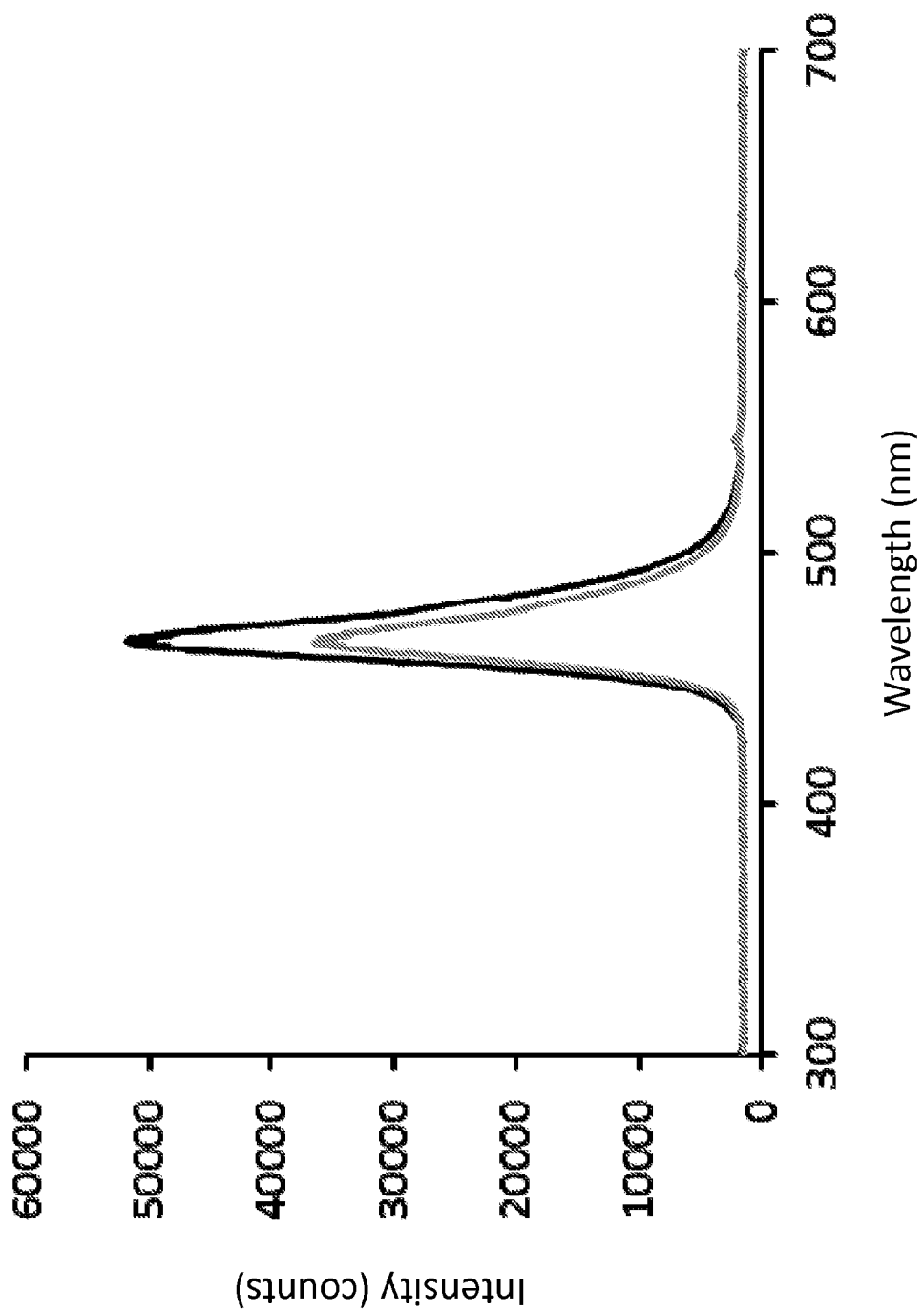
FIG. 8 shows a comparison of the spectra of light from a VAOL-5GSBY4 LED (λdominant=460 nm) LED directed through 500 μm poly(methylmethacrylate) (PMMA) optical fiber that is clad (top trace) and light passing through the fiber after a region is declad (bottom trace).

FIG. 8 shows the spectrum of light from the VAOL-5GSBY4 LED ($\lambda_{dominant}$=460 nm) exiting the 500 μm PMMA optical fiber pre- and post-decladding. Measurements were made at 22° C. The loss in total counts of light reaching the detector (~51000 for the clad fiber and ~36000 for the declad fiber) after de-cladding indicated that light was in fact lost in the declad region of the fiber. Initiating the photolytic release of NO from SNAP-SR coated on the optical fibers used in this study required the creation of a region of excitance along the optical fiber where the otherwise totally internally reflected light could escape the core to interact with the donor molecules in the polymer coating. Given the same radiant intensity from a light source, a decrease in the transmittance through an optical fiber after the cladding removal process indicated that light was exiting the fiber in the declad region where it could then potentially interact with a donor coating. The spectra taken before cladding was removed (cladded) and spectra taken after removal (decladded) clearly demonstrated that the cladding removal process created a discrete region of excitance for NO generation.

Example 5

Figure 9:
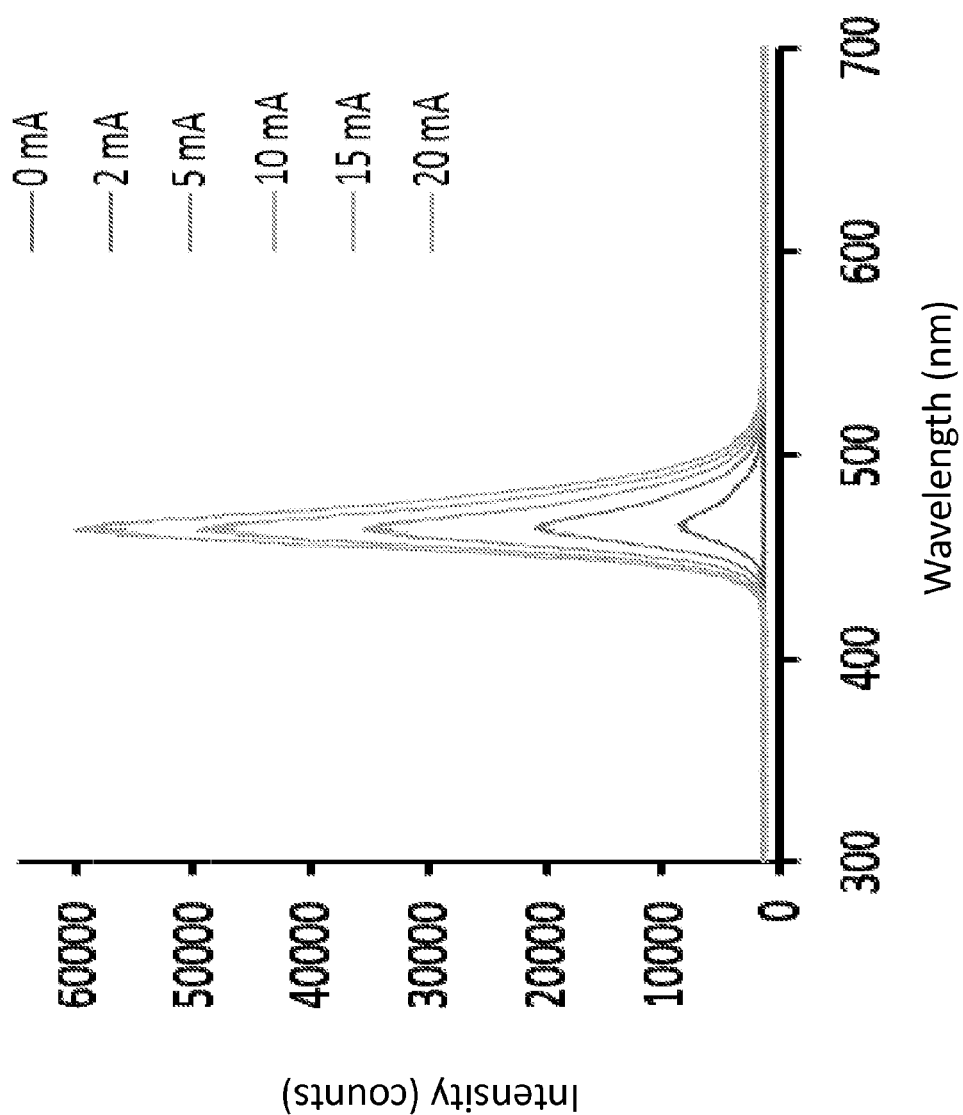
FIG. 9 shows the intensity and spectra of light generated from a VAOL-5GSBY4 LED (λdominant=460 nm) LED with changing drive current.
Figure 10:
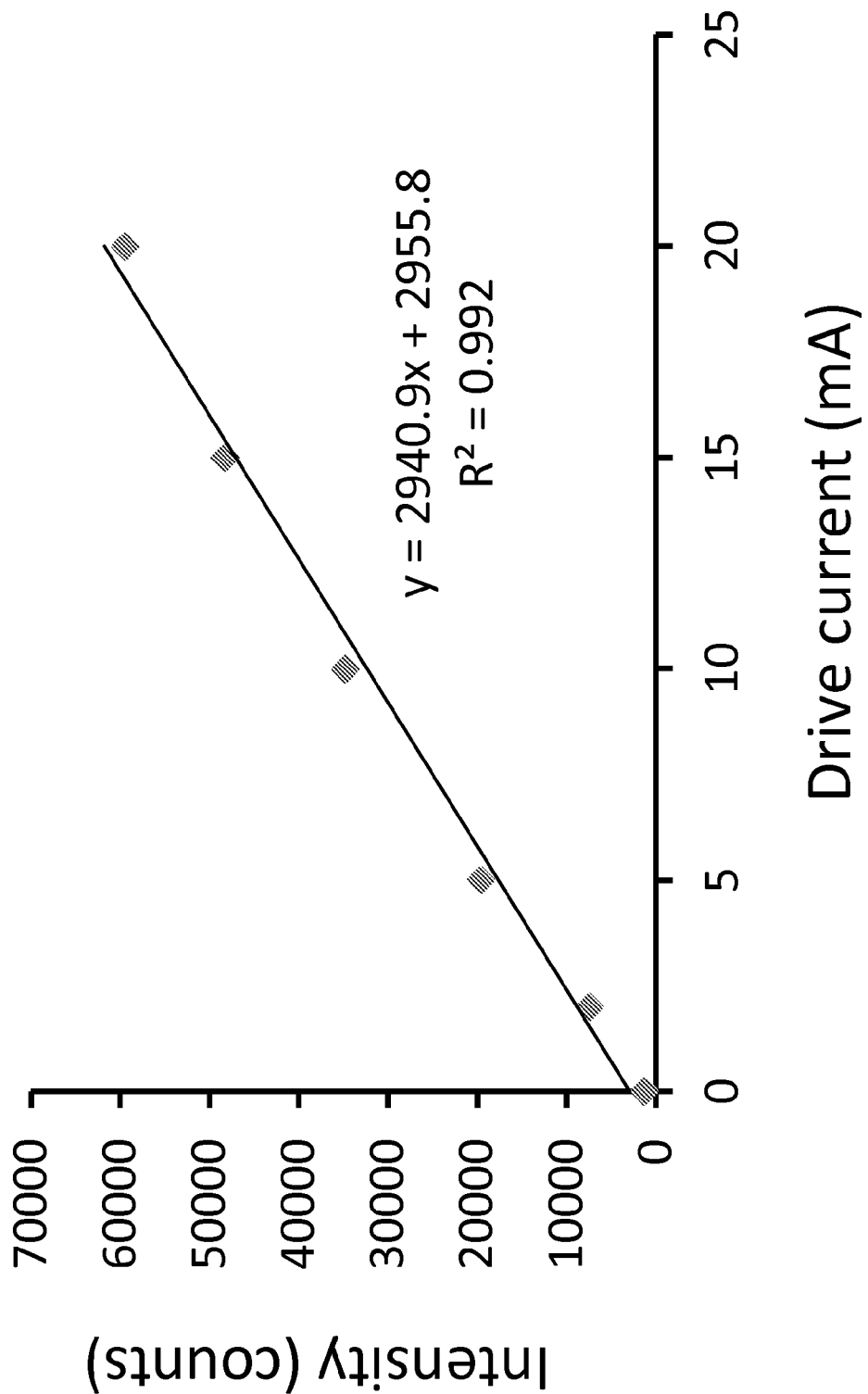
FIG. 10 shows the intensity of light generated from a VAOL-5GSBY4 LED (λdominant=460 nm) is linearly related to the varied drive current applied through the range used in this study.

Calibration Relates Forward Voltage to Drive Current and Light Output from LED The forward voltage ($V_{out}$) of a semiconductor based LED is typically dependent upon the drive current ($I_{drive}$) through it and can often be closely approximated as a first order linear relationship through the majority of its operating range. The source current to the excitatory LED ($I_{drive}$) used was in fact a product of a microcontroller which was wirelessly programmed to modulate voltage in a linear manner. An additional characteristic which semiconductor LEDs often demonstrate is a current dependent shift in dominant wavelength ($\lambda_d$). To determine the linearity and the current-dependent dominant wavelength, the spectra of light emitted by the LED at different currents were recorded through the operating range utilized and are shown in FIG. 9. FIG. 9 shows the intensity and spectra of light generated from a VAOL-5GSBY4 LED ($\lambda_{dominant}$=460 nm) LED with changing drive current. Measurements were made at 22° C. The resulting data demonstrated that the dominant wavelength of light produced by the LED did not shift with changing $I_{drive}$, and therefore the wavelength at which the NO donor was irradiated was not dependent upon the drive current to the excitatory LED. Only the intensity of the emitted light varies with changing drive current. The maximum irradiance of light output from the LED was also linear with change in $I_{drive}$, shown in FIG. 10 (Irrad.=2940$I_{drive}$+2960, $R^2$=0.992).

Example 6

Dynamically Controlled NO Generation from Coated Fibers

Figure 11:
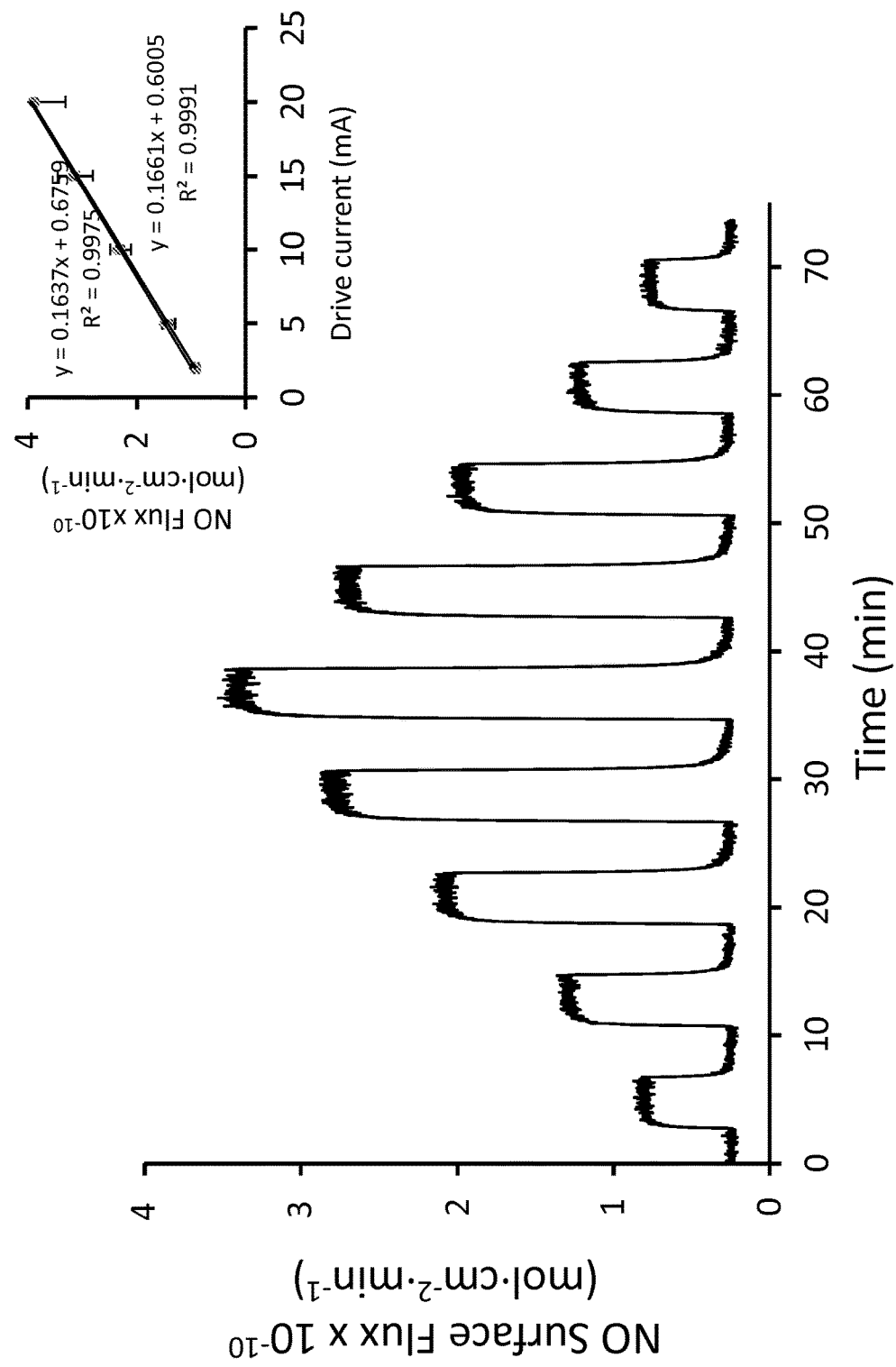
FIG. 11 shows NO generated from S-nitroso-N-acetylpenicillamine-polydimethylsiloxane (SNAP-PDMS) coated on declad region of a 500 μm poly(methylmethacrylate) (PMMA) optical fiber with drive current turned on and off and increasing with each step. The inset shows that the surface flux of NO generated is linearly related to the drive current applied to the LED illuminating the coated optical fiber and is identical whether $I_{drive}$ is applied form 0-20 mA or 20-0 mA.
Figure 12:
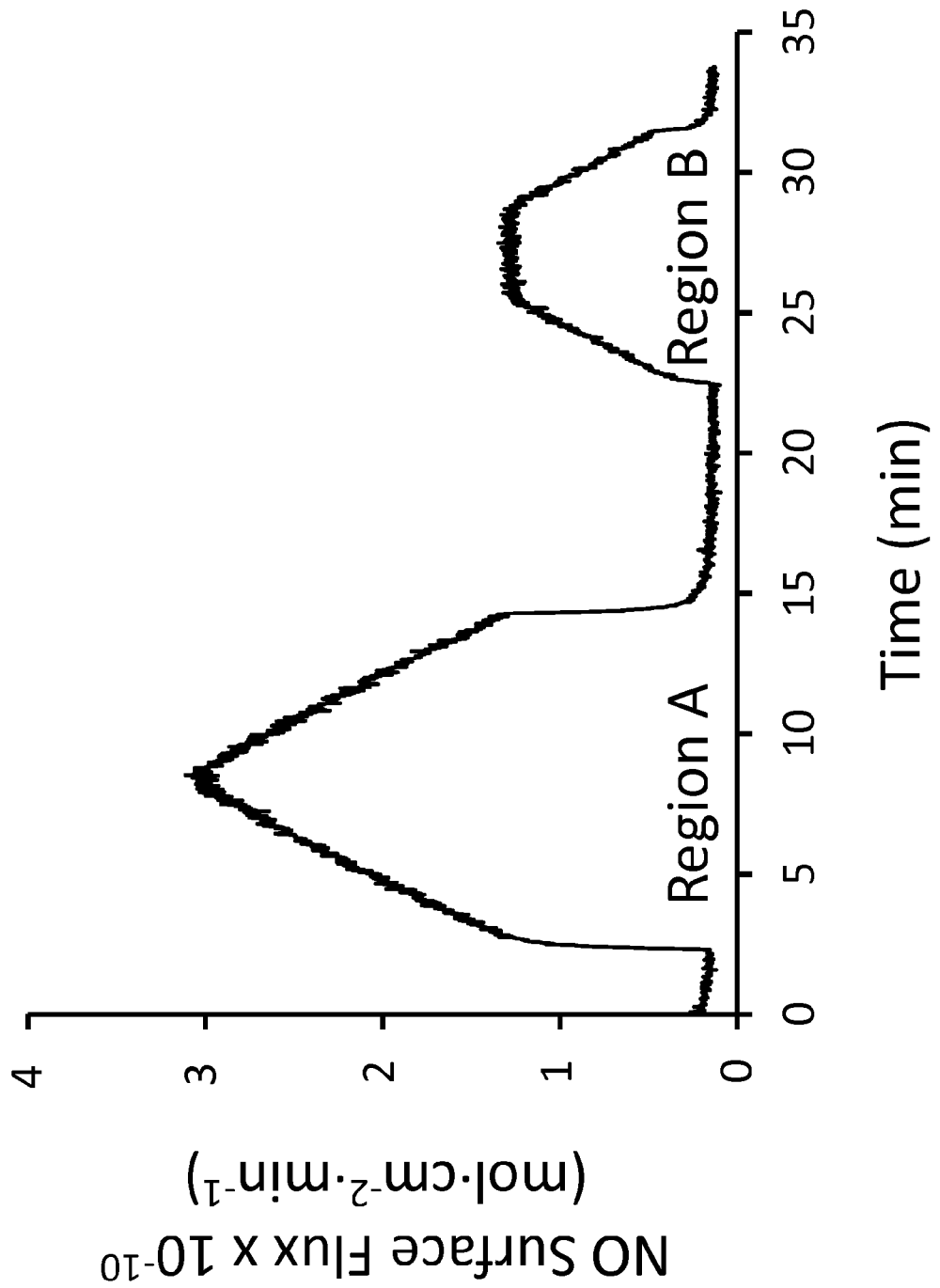
FIG. 12 shows the level of NO generated from the declad SNAP-PDMS coated PMMA fibers when the current applied to the LED was continuously ramped up and then down.

In order to examine the NO generating capability of the platform described herein, representative sequences were programmed and executed by the NO generating platform. FIG. 11 and FIG. 12 demonstrate that the profile of NO generation can predictably follow any sequence programmed by an investigator. The pattern of $I_{drive}$ generated and the subsequent NO surface flux produced in this example are listed in Table 1. The pulses used in this example were in 4 minute intervals, with light off and then light on with increasing $I_{drive}$ applied in each subsequent step from 2, 5, 10, 15, and 20 mA and then 15, 10, 5, 2, and 0 mA applied to the LED via the ED. The corresponding surface fluxes of NO generated were 0.95±0.04, 1.50±0.13, 2.37±0.33, 3.19±0.45, 3.88±0.57, 3.13±0.13, 2.30±0.19, 1.42±0.12, and 0.91±0.04 (all ×$10^{-10}$ mol·$cm^{-2}$·$min^{-1}$), respectively. Importantly, NO generation was also very repeatable over time (FIG. 11). FIG. 11 shows NO generated from S-nitroso-N-acetylpenicillamine-polydimethylsiloxane (SNAP-PDMS) coated on declad region of a 500 μm poly(methylmethacrylate) (PMMA) optical fiber with drive current turned on and off and increasing with each step. Measurements were made at 22° C. with chemiluminescence detection. The surface flux of NO generated from these SNAP-PDMS coated fibers was also linear with $I_{drive}$ as shown in FIG. 11 inset. The 2 lines shown in FIG. 11 inset compared the level of NO generated when the $I_{drive}$ was increased from 0 to 20 mA and the level of NO generated when progressing from 20 mA to 0 mA. The least-squares lines were statistically equivalent, indicating that the ability to calibrate and therefore control the level of NO generated from these fibers was reproducible and repeatable. Additionally, there was no bias introduced whether the $I_{drive}$ was increased from low to high or from high to low. To support the claim that the NO generated from this platform resulted from light exiting the core of the coated fiber at the declad region, a fiber was coated with SNAP-PDMS in the process previously described with the exception that the cladding was never removed. A pulsatile sequence with matching drive current and shorter duration was programmed and executed by the excitatory LED (grey trace FIG. 11). The results showed that NO generation from a fiber with cladding intact was dramatically attenuated. The small amount of NO generated was thought to result from a very small amount of programmed light exiting the cut end of the fiber and interacting with the coated SNAP-PDMS.

TABLE 1

Listing of the drive current ($I_{drive}$) applied to the VAOL-5GSBY4 LED used to illuminate the SNAP-PDMS coated fiber, the duration it was applied and resulting surface flux of NO generated.

| $I_{drive}$ (mA) | Duration (min) | NO Surface Flux (×$10^{-10}$ mol · $cm^{-2}$ · $min^{-1}$) |
|---|---|---|
| 0 | 4 | |
| 2 | 4 | 0.95 ± 0.04 |
| 0 | 4 | |
| 5 | 4 | 1.50 ± 0.13 |
| 0 | 4 | |
| 10 | 4 | 2.37 ± 0.33 |
| 0 | 4 | |
| 15 | 4 | 3.19 ± 0.45 |
| 0 | 4 | |

TABLE 1-continued

Listing of the drive current ($I_{drive}$) applied to the VAOL-5GSBY4 LED used to illuminate the SNAP-PDMS coated fiber, the duration it was applied and resulting surface flux of NO generated.

| $I_{drive}$ (mA) | Duration (min) | NO Surface Flux ($\times 10^{-10}$ mol · cm$^{-2}$ · min$^{-1}$) |
|---|---|---|
| 20 | 4 | 3.88 ± 0.57 |
| 0 | 4 | |
| 15 | 4 | 3.13 ± 0.32 |
| 0 | 4 | |
| 10 | 4 | 2.30 ± 0.19 |
| 0 | 4 | |
| 5 | 4 | 1.42 ± 0.12 |
| 0 | 4 | |
| 2 | 4 | 0.91 ± 0.04 |
| 0 | 4 | |

FIG. 12 shows NO generated from S-nitroso-N-acetylpenicillamine-polydimethylsiloxane (SNAP-PDMS) coated on 500 µm poly(methylmethacrylate) (PMMA) optical fiber with drive current turned on and steadily increased, then decreased at the same rate and turned off, followed by a steady increase in drive current, current held constant and then the decreased. Measurements were made at 22° C. with chemiluminescence detection. The pattern of light applied to these fibers in Region A of the trace was programmed to hold an $I_{drive}$ of 0 that stepped up 5 mA, ramped at a rate of 3% applied current/20 sec for 6 min (stopping at 15 mA) and then ramping back down at a rate of –3% applied current/20 sec for 6 min (stopping to 5 mA) followed by stepping down to 0 mA applied for 4 min. The second region (Region B) then started with $I_{drive}$ stepping up to 2 mA, ramped at a rate of 3% applied current/20 sec for 3 min (stopping at 5 mA), $I_{drive}$ was then held constant for 3 min and then decreased at a rate of –3% applied current/20 sec for a duration of 3 min (stopping at 2 mA), followed by stepping down to 0 mA (i.e., light turned off) (the programmed sequence of drive current is listed Table 2). The level of NO generated corresponded to a surface flux of 1.64 to 3.66 back to 1.64×10$^{-10}$ mol·cm$^{-2}$·min$^{-1}$ for region A while a non-zero $I_{drive}$ was applied and then an NO surface flux of 0.41 to 1.64, held at 1.64 for 5 min and then back to 0.41×10$^{-10}$ mol·cm$^{-2}$·min$^{-1}$ in region B This showed that if $I_{drive}$ was changed at a constant rate, the level of NO generated also changed at the same constant rate and if $I_{drive}$ was held constant, then the level of NO generated was also maintained at a constant level. FIG. 11 and FIG. 12 clearly demonstrate that the level and pattern of NO generated from these SNAP-PDMS coated optical fibers can be continuously and dynamically controlled with precision by wirelessly changing the $I_{drive}$ that is used to control the LED.

TABLE 2

Listing of the programmed sequence of the initial drive current ($I_{drive}$) applied and the ending drive current when changing the current applies at a linear rate of 3%/20 sec to the VAOL-5GSBY4 LED used to illuminate the SNAP-PDMS coated fiber and the duration the current was applied.

| Initial $I_{drive}$ (mA) | Ending $I_{drive}$ (mA) | Duration (min) |
|---|---|---|
| 0 | 0 | 3 |
| 5 | 15 | 6 |
| 15 | 5 | 6 |
| 0 | 0 | 8 |
| 2 | 5 | 3 |
| 5 | 5 | 3 |

TABLE 2-continued

Listing of the programmed sequence of the initial drive current ($I_{drive}$) applied and the ending drive current when changing the current applies at a linear rate of 3%/20 sec to the VAOL-5GSBY4 LED used to illuminate the SNAP-PDMS coated fiber and the duration the current was applied.

| Initial $I_{drive}$ (mA) | Ending $I_{drive}$ (mA) | Duration (min) |
|---|---|---|
| 5 | 2 | 3 |
| 0 | 0 | 2 |

Figure 13:
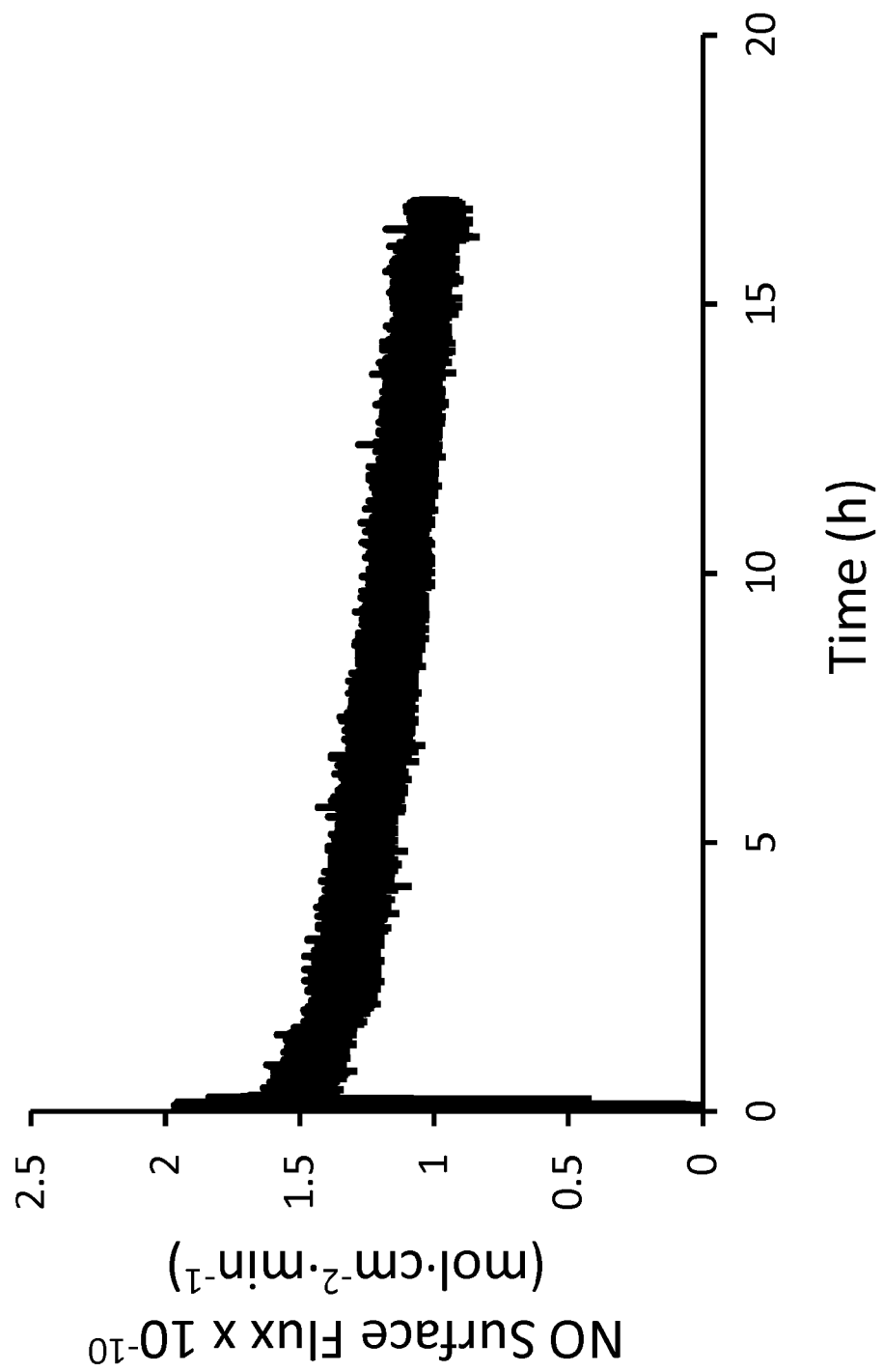
FIG. 13 shows NO release from a SNAP-PDMS coated optical fiber with the 5 mA drive current applied at a constant level for 17 hours at 22° C.
Figure 14:
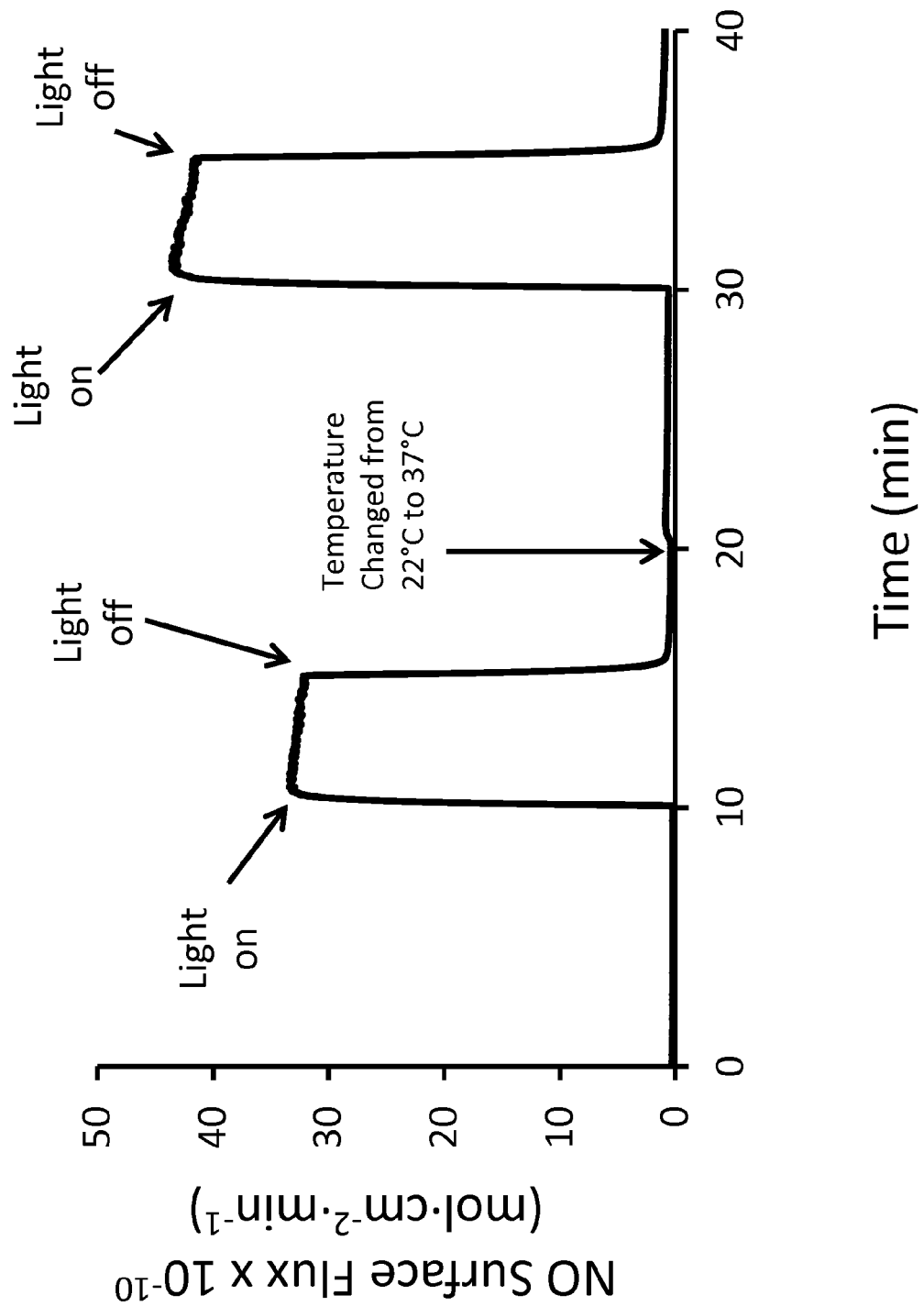
FIG. 14 illustrates the temperature effect on NO release from a 12 mm diameter disc of SNAP-PDMS (300 μm thick) with no light and illuminated with a 460 nm LED with a drive current of 10 mA at 22° C. and at 37° C. with chemiluminescence detection.

FIG. 13 shows the surface flux of NO that was generated over a 17 h period when the drive current to the LED was held at a constant 5 mA. Measurements made at 22° C. with chemiluminescence detection. The surface flux of NO decreased from an initial level of ~1.5 to ~1.0×10$^{-10}$ mol·cm$^{-2}$·min$^{-1}$, respectively. This was an approximate decrease of 30% over the 17 h period. The total amount of NO that could be delivered from the coated fibers depended on several variables. The illumination pattern used affected how quickly the RSNO reservoir was depleted. The thickness of the SNAP-PDMS coating and the concentration of SNAP incorporated into the material determined the total amount of RSNO available. Additionally, elevated temperature also caused an increase in the level of NO generated from the polymer. The effect of increasing the temperature from 22° C. (the temperature at which data presented in FIGS. 11-13 were collected) to 37° C. is shown in FIG. 14. A 12 mm diameter disc of SNAP-PDMS (300 µm thick) was protected from light, then illuminated with a 460 nm LED (10 mA drive current) held 5 cm directly above the films at 22° C. and then the temperature was raised to 37° C. Measurements were made with chemiluminescence detection. The level of NO released with no light illuminating the disc was ~0.23×10$^{-10}$ mol·cm$^{-2}$·min$^{-1}$ at 22° C. and when the light was turned on, the level of NO increased to ~33×10$^{-10}$ mol·cm$^{-2}$·min$^{-1}$ When the temperature was increased to 37° C., the corresponding NO release with no light and illuminated from the same film was ~0.78 and ~43×10$^{-10}$ mol·cm$^{-2}$·min$^{-1}$, respectively. The surface flux obtained from the disc was greater than that obtained from the fibers at the same drive current for several reasons. First, the SNAP-PDMS disc was 3 times as thick as the coating on the fiber, and the LED was illuminating the polymer with bulk radiation, thereby initiating NO release from the entire thickness of the material at the same time while the coated fibers illuminated the polymer with a leaky evanescent wave that delivered a much lower level of irradiation.

Figure 15:
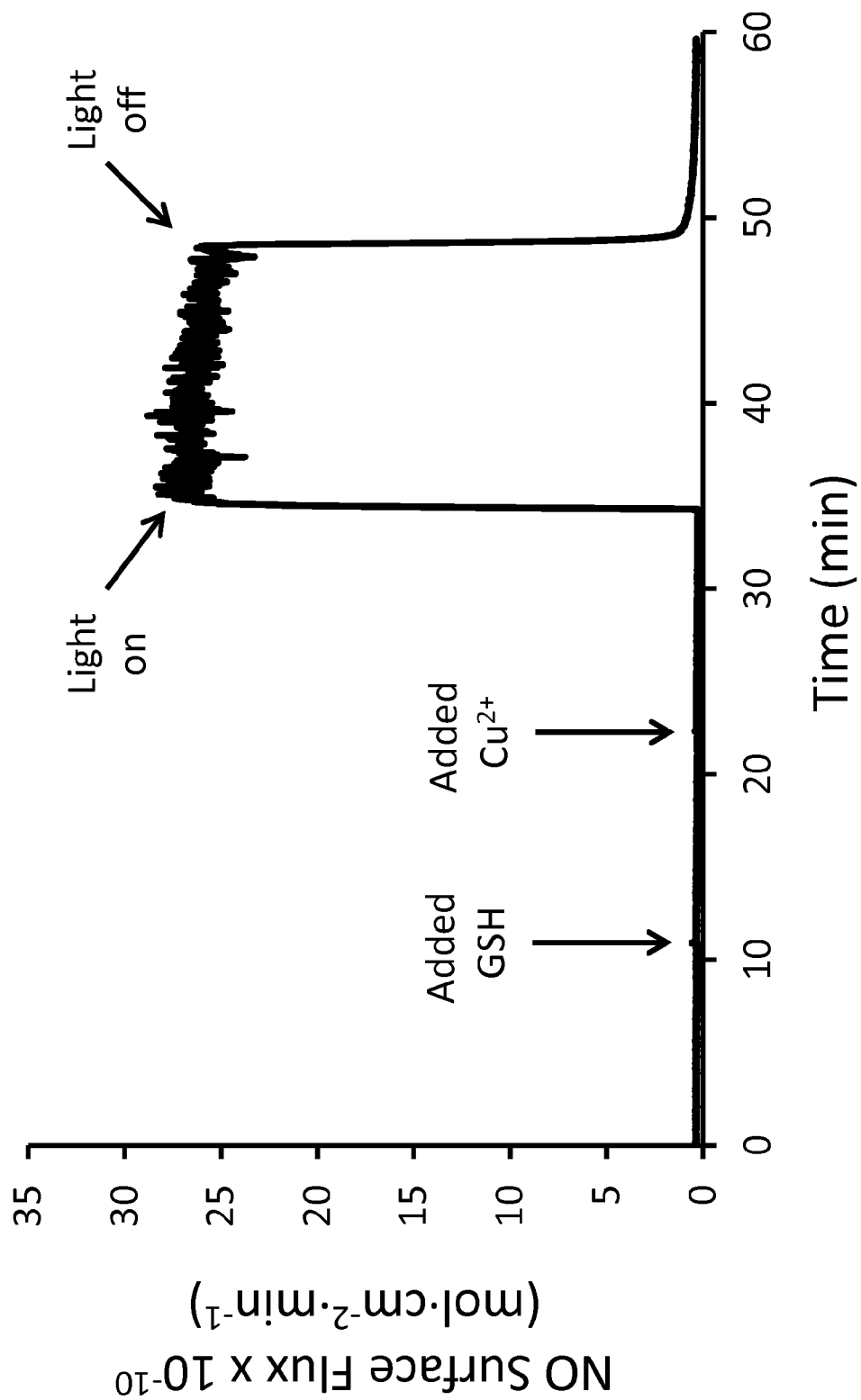
FIG. 15 illustrates NO release from a 12 mm diameter disc of SNAP-PDMS (300 μm thick) top coated with Dow-Corning RTV-3140 is not effected by glutathione and copper ions in bathing solution when polymer is protected from light.

The use of PDMS as the base polymer in this NO-releasing material contributed to the controlled release of NO from the system. PDMS is a hydrophobic polymer that excluded ions from diffusing into polymer matrix and prematurely decomposing the SNAP covalently linked to the polymer. This may be important when considering the abundant species present in the physiological environment that are known to decompose RSNOs (i.e., cysteine, glutathione, trace metal ions, etc.). FIG. 15 shows NO release from a 12 mm disc of SNAP-PDMS top coated with Dow Corning RTV-3140 PDMS and soaked in PBS, 5 mM glutathione, and 5 mM glutathione with 250 mM CuBr$_2$, while excluding light. No NO was released from the film until a 460 nm LED (10 mA drive current) was used to illuminate the polymer film from a fixed distance of 5 cm. Measurements were made at 22° C. with chemiluminescence detection. This clearly demonstrated that the PDMS polymer base was able to prevent ions from causing decomposition of the SNAP and indicated that controlled release should be maintained when used in vivo.

As shown herein, fluxes of NO in the range of estimated physiologic relevance were generated from SNAP-PDMS coated onto prepared optical fibers, and the profile of NO flux generated in this way were directed by an investigator using a novel hardware and software platform that wirelessly controlled light produced from an LED coupled to the coated optical fiber. There are no published studies evaluating the biologic response to variable and controlled schemes of NO generation beyond constant, continuous fluxes. However, it is known that the host response seen by sensors placed either intravascularly or subcutaneously may vary over time. Thus, the flux of NO which best inhibits or mediates these responses may vary over time as well. Fine tuning the release of NO to an ideal level on a temporal basis by modulating the $I_{drive}$ applied to an LED could abate the host response to indwelling sensors prepared with NO generating materials over a meaningful duration, thereby improving biological response toward indwelling sensors and increasing their analytical performance and clinically viability.

Example 7

Generation of a SNAP-PVC Polymer

In order to create a SNAP-PVC polymer with the SNAP covalently linked to the backbone structure, 1.637 g of PVC (MW=233,000) was suspended in 40 Ml of methanol. An abundant amount of ethylenediamine (EDA) (10 Ml) and 40 Ml of methanol were placed in a flask and heated to 65° C. for 4 hours. The product was then filtered and washed with methanol, distilled water, 1 M HCl, distilled water, and methanol again (in that specific order). The following product, PVC-NH$_2$, was then dissolved in tetrahydrofuran, and the self-protected thiolactone was added and stirred overnight at room temperature. The resultant exposed thiol groups were nitrosated by using t-butyl nitrite to form SNAP-PVC.

Example 8

Generation of a SNAP-PU Polymer

The SNAP will be covalently linked to polyurethane is as follows. 15 g of Pellethane (or other PU) is dissolved in 300 mL N,N-dimethylacetamide (DMA) and cooled to −6° C. in dry ice/carbon tetrachloride bath. 15 mL of 1,4-dibromobutane is added with addition of 7.6 mL 1 M lithium t-butoxide in hexane dissolved in 20 mL DMA dropwise over 10 min period. The reaction is stirred for 1 h in standard ice bath. Lithium t-butoxide is quenched by the addition of 6.5 mL acetic acid. The resultant material is poured into 1 L cold methanol and allowed to stand for 2 hours and come to room temperature. The resultant solid is washed with fresh methanol and vacuum dried. The compound is then dissolved in DMA, and 20 mL of ethylenediamine (EDA) is added and stirred for 4-6 hours. The derivatized Pellethane is washed in methanol and allowed to dry. The aminated Pellethane is then dissolved in DMA, and the self-protected thiolactone is added and stirred overnight at room temperature. The resultant exposed thiol groups are nitrosated by using t-butyl nitrite to form SNAP-PU. The amination of these polymers is readily applicable to aminating the urethane linkage of all PUs. Once pendant primary amines are introduced onto the backbone of the polymer, SNAP can be covalently linked via the self-protected thiolactone. The more hydrophobic the PU, the more stable the SNAP is in the polymer matrix.

Example 9

Use of Polymers in Medical Dressings

A polymer described herein, such as SNAP-PDMS, SNAP-PVC, or SNAP-PU, is used in the synthesis of a medical dressing, such as TEGADERM™ (3M, St. Paul, Minn.). The dressing is used to cover and protect wounds and catheter sites. Advantages of the medical dressing include its breathability and conformation to the skin such that it adheres in places such as the fingers and toes. Incorporation of polymers described herein into the medical dressing renders the dressing biocompatible. The polymer releases NO, thereby decreasing fibrous encapsulation, enhancing wound healing, and improving tissue response.

Example 10

Use of Polymers in Medical Tubing

A polymer described herein, such as SNAP-PDMS, SNAP-PVC, or SNAP-PU, is used in the synthesis of medical tubing, such as those used for intravenous tubes and catheters. Incorporation of polymers described herein into the medical dressing renders the dressing biocompatible. The polymer releases NO, thereby decreasing fibrous encapsulation, enhancing wound healing, and improving tissue response.

Example 11

Use of Polymers in Medical Device Coatings

A polymer described herein, such as SNAP-PDMS, SNAP-PVC, or SNAP-PU, is used to coat a medical device such as a pacemaker or implantable glucose monitor. Coating the device with polymers described herein into the medical dressing renders the dressing biocompatible. The polymer releases NO, thereby decreasing fibrous encapsulation, enhancing wound healing, and improving tissue response.

What is claimed is:
1. A compound of Formula (II):

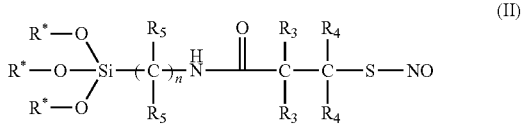

and racemates, enantiomers and diastereomers thereof;
wherein:
R* is a polysiloxane;
each $R_3$ is independently selected from H and aminocarbonyl, at least one $R_3$ is an aminocarbonyl;
each $R_4$ is independently selected from $C_{1-4}$ alkyl;
each $R_5$ is H;
and
n is 1 to 6.

2. The compound according to claim 1, wherein n is 3.

3. The compound according to claim 1, wherein one $R_3$ is —NHC(O)CH$_3$.

4. The compound according to claim 3, wherein the other $R_3$ is H.

5. The compound according to claim 1, wherein both $R_4$ are methyl.

6. A medical device comprising a composition comprising the compound according to claim 1.

7. The medical device of claim 6, wherein at least a portion of the medical device is fabricated from the composition.

8. The medical device of claim 7, wherein the portion defines an outer surface of the medical device.

9. The medical device of claim 8, wherein the medical device is coated with the composition.

10. A method for improving the biocompatibility of a medical device, comprising, coating the medical device with a composition comprising the compound according to claim 1.

* * * * *